(12) United States Patent
Uehara

(10) Patent No.: US 12,230,012 B2
(45) Date of Patent: Feb. 18, 2025

(54) MACHINE LEARNING SYSTEM AND METHOD, INTEGRATION SERVER, INFORMATION PROCESSING APPARATUS, PROGRAM, AND INFERENCE MODEL CREATION METHOD

(71) Applicant: FUJIFILM Corporation, Tokyo (JP)

(72) Inventor: Daiki Uehara, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 384 days.

(21) Appl. No.: 17/722,383

(22) Filed: Apr. 17, 2022

(65) Prior Publication Data

US 2022/0237898 A1    Jul. 28, 2022

Related U.S. Application Data

(63) Continuation of application No. PCT/JP2020/038694, filed on Oct. 14, 2020.

(30) Foreign Application Priority Data

Oct. 23, 2019 (JP) ................................ 2019-192548

(51) Int. Cl.
  *G06V 10/774* (2022.01)
  *G06N 3/044* (2023.01)
  (Continued)

(52) U.S. Cl.
  CPC ........... *G06V 10/774* (2022.01); *G06N 5/022* (2013.01); *G06V 10/764* (2022.01);
  (Continued)

(58) Field of Classification Search
  None
  See application file for complete search history.

(56) References Cited

U.S. PATENT DOCUMENTS

| 11,461,690 | B2 * | 10/2022 | Szeto | G06N 20/10 |
| 2018/0330819 | A1 * | 11/2018 | Weschler | G16B 50/30 |
| 2019/0279082 | A1 * | 9/2019 | Moloney | G06V 10/82 |

FOREIGN PATENT DOCUMENTS

| CN | 1547721 A | * | 11/2004 | ............. G06F 19/32 |
| WO | WO-2013009024 A2 | * | 1/2013 | ............ G06F 19/322 |

(Continued)

OTHER PUBLICATIONS

H. Brendan Mcmahan et al., "Communication-Efficient Learning of Deep Networks from Decentralized Data," arXiv:1602.05629v3, Feb. 2017, pp. 1-11.

(Continued)

*Primary Examiner* — Mohammed Rachedine
(74) *Attorney, Agent, or Firm* — JCIPRNET

(57) ABSTRACT

Provided are a machine learning system and method, an integration server, an information processing apparatus, a program, and an inference model creation method capable of solving a problem caused by non-uniform quality of learning data in federated learning and improving an inference accuracy of a model. Each of a plurality of client terminals classifies data stored in a medical institution based on a data acquisition condition and classifies learning data into each data group acquired under the same or a similar acquisition condition. Each client terminal executes machine learning of a learning model for each learning data group classified into each condition category and transmits each learning result and condition information to an integration server. The integration server integrates received learning results for each condition category to create a plurality of master model candidates and evaluates the inference accuracy of each master model candidate.

24 Claims, 9 Drawing Sheets

(51) Int. Cl.
*G06N 3/045* (2023.01)
*G06N 3/063* (2023.01)
*G06N 3/08* (2023.01)
*G06N 5/022* (2023.01)
*G06V 10/764* (2022.01)
*G06V 10/776* (2022.01)
*G06V 10/82* (2022.01)
*G16H 30/40* (2018.01)
*G16H 50/20* (2018.01)

(52) U.S. Cl.
CPC ............ *G06V 10/776* (2022.01); *G06V 10/82* (2022.01); *G06V 2201/03* (2022.01)

(56) References Cited

FOREIGN PATENT DOCUMENTS

| WO | WO-2016152476 A1 * | 9/2016 | ........... G06F 19/322 |
|---|---|---|---|
| WO | WO-2018152366 A1 * | 8/2018 | ............ G06Q 30/04 |
| WO | 2019170785 | 9/2019 | |
| WO | WO-2020006495 A1 * | 1/2020 | ........... G06F 40/205 |

OTHER PUBLICATIONS

Micah J Sheller et al., "Multi-Institutional Deep Learning Modeling Without Sharing Patient Data: A Feasibility Study on Brain Tumor Segmentation," arXiv:1810.04304v2, Oct. 2018, pp. 1-14.

Li Huang et al., "Patient clustering improves efficiency of federated machine learning to predict mortality and hospital stay time using distributed electronic medical records," Journal of Biomedical Informatics, vol. 99, Sep. 2019, pp. 1-13.

Avishek Ghosh et al., "Robust Federated Learning in a Heterogeneous Environment," arXiv:1906.06629v2, Oct. 2019, pp. 1-26.

"International Search Report (Form PCT/ISA/210) of PCT/JP2020/038694," mailed on Nov. 24, 2020, with English translation thereof, pp. 1-5.

"Written Opinion of the International Searching Authority (Form PCT/ISA/237)" of PCT/JP2020/038694, mailed on Nov. 24, 2020, with English translation thereof, pp. 1-8.

* cited by examiner

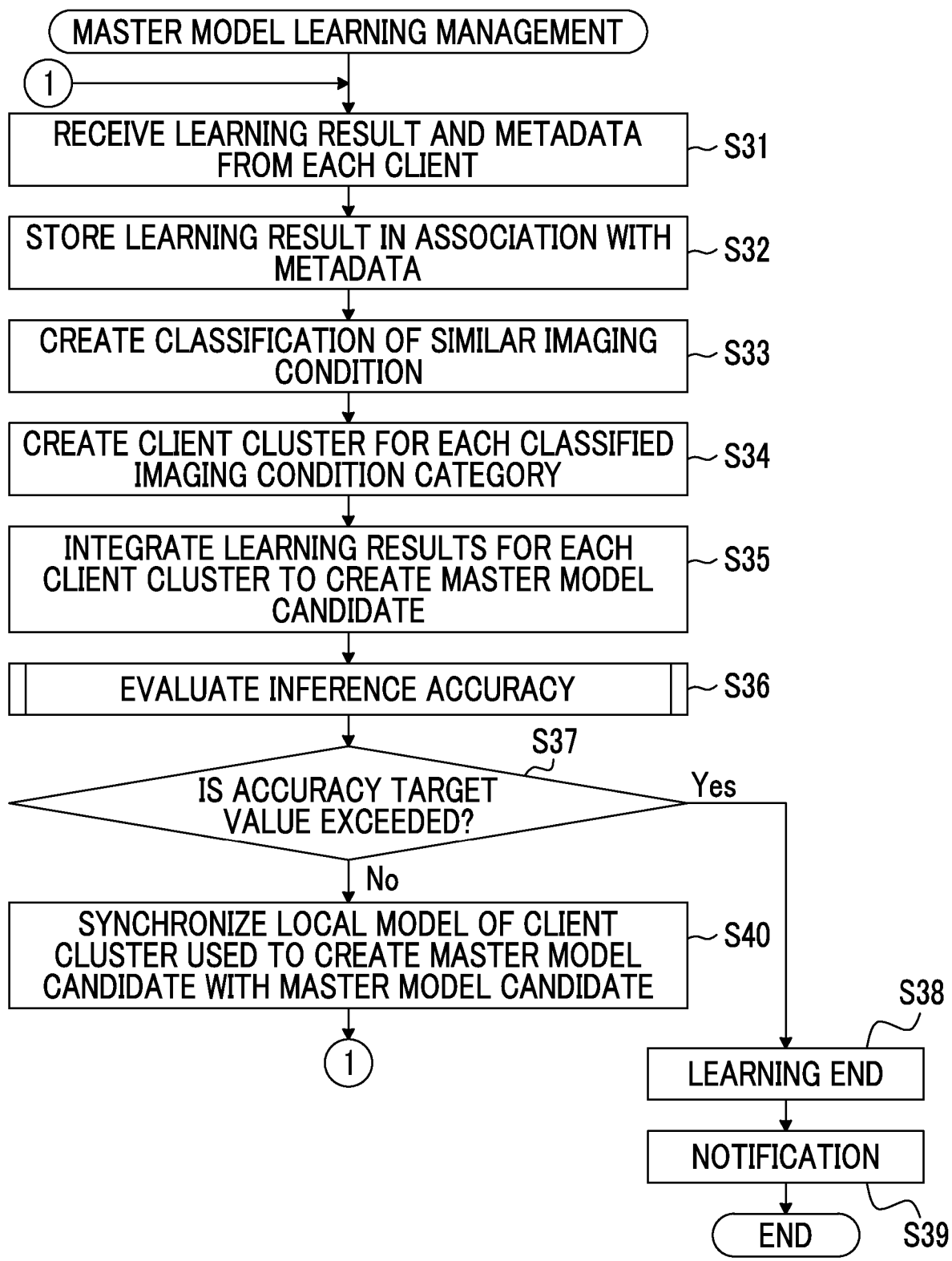

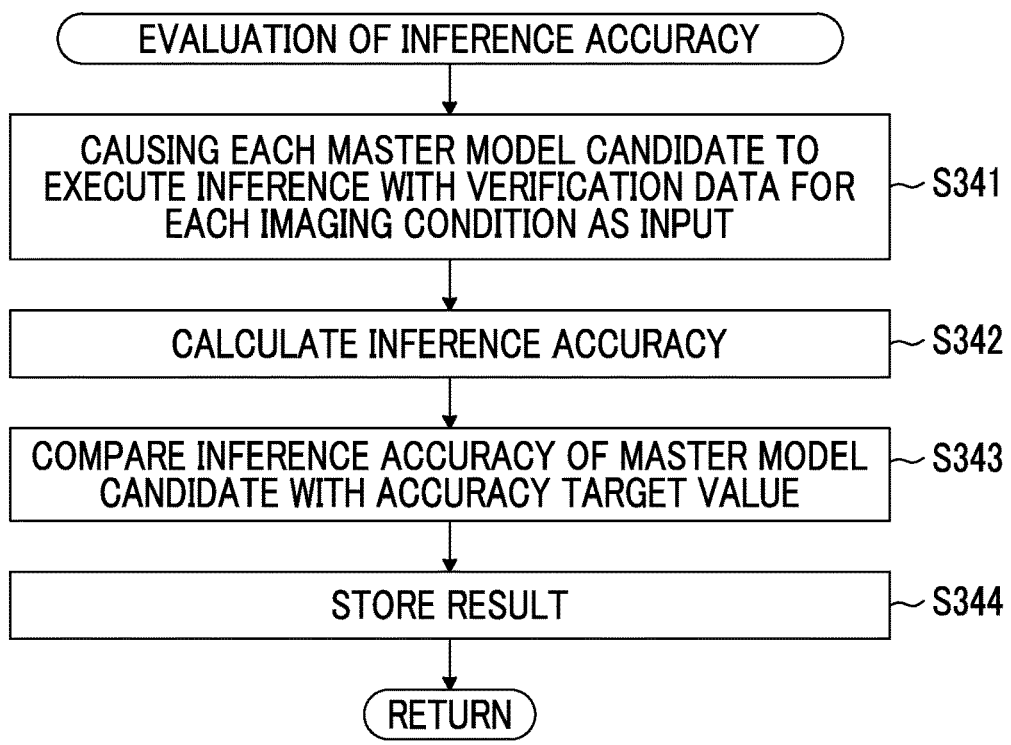
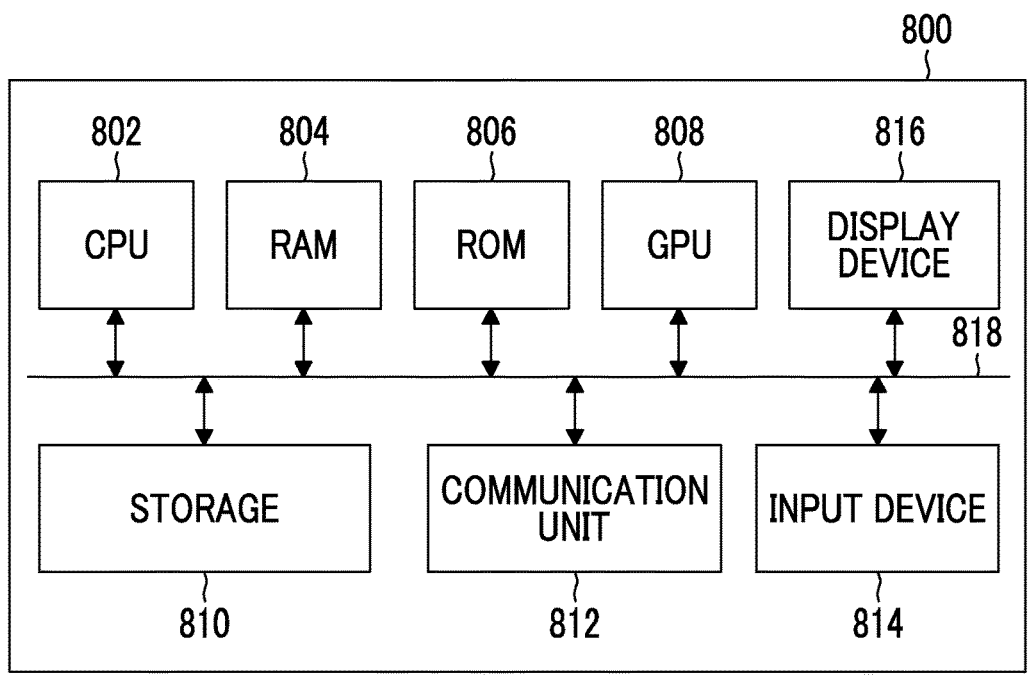

MACHINE LEARNING SYSTEM AND METHOD, INTEGRATION SERVER, INFORMATION PROCESSING APPARATUS, PROGRAM, AND INFERENCE MODEL CREATION METHOD

CROSS-REFERENCE TO RELATED APPLICATIONS

The present application is a Continuation of PCT International Application No. PCT/JP2020/038694 filed on Oct. 14, 2020 claiming priority under 35 U.S.C. § 119(a) to Japanese Patent Application No. 2019-192548 filed on Oct. 23, 2019. Each of the above applications is hereby expressly incorporated by reference, in its entirety, into the present application.

BACKGROUND OF THE INVENTION

1. Field of the Invention

The present invention relates to a machine learning system and method, an integration server, an information processing apparatus, a program, and an inference model creation method, and particularly relates to a machine learning technique using a federated learning mechanism.

2. Description of the Related Art

In development of medical artificial intelligence (AI) using deep learning, it is necessary to train an AI model. However, for this learning, it is necessary to extract learning data such as a diagnosis image from a medical institution to an external development site or to an external development server. For this reason, there are few medical institutions that can cooperate in providing learning data. Further, even in a case where learning data is provided from a medical institution, there is always a privacy-related risk.

On the other hand, in a case where a federated learning mechanism is used, a federated learning mechanism being proposed in H. Brendan McMahan, Eider Moore, Daniel Ramage, Seth Hampson, and Blaise Agüera y Arcas, "Communication-Efficient Learning of Deep Networks from Decentralized Data", arXiv:1602.05629v3 [cs.LG], 28 Feb. 2017, learning is performed on a terminal in which data for training exists, and only a weight parameter of a network model that is a learning result on each terminal is transmitted from a terminal group to an integration server. That is, in federated learning, learning data is not provided to the integration server side, and only data of the learning result on each terminal is provided from the terminal side to the integration server side.

For this reason, learning can be performed without extracting data that requires consideration for privacy to the outside. Thus, federated learning is a technique that has been attracting attention in recent years.

In Micah J Sheller, G Anthony Reina, Brandon Edwards, Jason Martin, and Spyridon Bakas, "Multi-Institutional Deep Learning Modeling Without Sharing Patient Data: A Feasibility Study on Brain Tumor Segmentation", arXiv: 1810.04304v2 [cs.LG], 22 Oct. 2018, a result of an example in which federated learning is applied to development of a medical AI is reported.

SUMMARY OF THE INVENTION

In a case where federated learning is used for development of a medical AI, it is not necessary to extract data such as a diagnosis image. However, contents of the data held by each medical institution vary, and learning environments are different for each client. As a result, results of learning performed by each client also vary. For example, in a case where an AI model for medical image diagnosis is created by an unspecified large number of medical institutions participating in learning, issues are that imaging conditions are not constant for each image, setting criteria for the imaging conditions are different for each medical institution, and thus there is no specific nature of noise on the image. This fact makes it difficult to separate, in a case where an inference accuracy of the AI model is not improved that much by learning in a case where the AI model for medical image diagnosis is created, whether a cause of the problem is noise or the model itself. The nature of noise changes depending on various conditions such as settings at the time of imaging. Therefore, it is difficult to develop a general-purpose and effective noise removal method.

In the existing federated learning mechanism, there is no index regarding client selection, such as how to select clients used for the learning from a large number of clients. In a case where the clients used for the learning are randomly selected from the client population in the federated learning mechanism, the above problem caused by images with different imaging conditions still occurs.

That is, due to the cause such as the difficult noise removal by various changes in the imaging conditions for each inspection image or non-uniform quality of learning images, it may be difficult to improve the inference accuracy of the model in a case where the training of the AI model is performed.

Such a problem is not limited to the AI model for medical images, but is also a common problem for an AI model that uses data other than images such as electrocardiogram waveform data. The term "imaging condition" can be extended to a term such as "inspection condition" or "data acquisition condition".

The present invention has been made in view of such circumstances, and an object of the present invention is to provide a technique of solving a problem caused by non-uniform quality of learning data in a case where a federated learning mechanism for performing training of an AI model can be implemented without extracting personal information such as a diagnosis image that requires consideration for privacy from a medical institution to the outside, and to provide a machine learning system and method, an integration server, an information processing apparatus, a program, and an inference model creation method capable of improving an inference accuracy of a model.

A machine learning system according to one aspect of the present disclosure includes a plurality of client terminals and an integration server. Each of the plurality of client terminals includes a learning data classification processing unit that classifies data stored in a data storage apparatus of a medical institution based on an acquisition condition of the data to classify learning data into each data group acquired under the same or a similar acquisition condition, a learning processing unit that executes machine learning of a learning model for each learning data group classified by the learning data classification processing unit into each condition category of the same or a similar acquisition condition, and a transmission unit that transmits learning results of the learning model executed for each learning data group and condition information regarding the acquisition condition of the learning data group used for the learning, to the integration server. The integration server includes a trained master model, a synchronization processing unit that synchronizes the learning model of each client terminal side with the master model before each of the plurality of client terminals trains the learning model, a reception unit that receives the learning results of the learning model and the condition information from each of the plurality of client terminals, a classification processing unit that classifies the learning results into each condition category, a master model candidate creation unit that integrates the learning results for each condition category to create a plurality of master model candidates, and an accuracy evaluation unit that evaluates an inference accuracy of each of the plurality of master model candidates.

According to the present aspect, the learning data group classified into each condition category based on the data acquisition condition is a collection of the data obtained under substantially uniform conditions in which data acquisition conditions fall into a category of the same or a similar condition. Each client terminal performs the training of each learning model for each condition category using the learning data group classified into each condition category and transmits each learning result and condition information to the integration server. The integration server classifies the received learning results into each condition category and integrates the learning results for each condition category to create the plurality of master model candidates. With the evaluation of the inference accuracy of each of the plurality of master model candidates created in this way, it is possible to extract a model with good inference accuracy.

According to the present aspect, the data of the learning data group used for the learning is homogenized, and thus effective learning can be performed.

The term "plurality of client terminals" may be an unspecified large number of client terminals. The client terminal may be configured to include a "data storage apparatus of a medical institution", or the "data storage apparatus of a medical institution" and the "client terminal" may be separate apparatuses.

For the term "data acquisition condition", the "acquisition condition" may be, for example, a type of apparatus used to generate the data and some or all of the various parameters set in the apparatus may be paraphrased as a "generation condition". The term "condition category" includes the concept of terms such as a condition division, a condition classification label, a condition type, a condition frame, and a condition range. The condition category may be set with including a range of a similar acquisition condition or may be set without including the range of a similar acquisition condition. The description "the same or a similar acquisition condition" may include only the same acquisition condition or may include the same and similar acquisition condition.

In the machine learning system according to another aspect of the present disclosure, the data may include an image captured by using an imaging apparatus, and the acquisition condition may include an imaging condition for the image.

In the machine learning system according to still another aspect of the present disclosure, the imaging condition may include a condition regarding a model of the imaging apparatus used for imaging.

The condition regarding the model of the imaging apparatus may be specified by, for example, a model name and/or a model number of the imaging apparatus.

In the machine learning system according to still another aspect of the present disclosure, the imaging condition may include a condition of an imaging parameter settable at a time of imaging.

The imaging parameter includes, for example, a radiation dose. The imaging condition may be a combination of a plurality of conditions.

In the machine learning system according to still another aspect of the present disclosure, the data may include inspection data acquired by using an inspection apparatus, and the acquisition condition may include an inspection condition under which the inspection data is acquired.

The imaging apparatus is a form of the inspection apparatus.

In the machine learning system according to still another aspect of the present disclosure, the acquisition condition may include a condition regarding a value of a parameter settable in an apparatus used to obtain the data, and the learning data classification processing unit may classify acquisition conditions in which a specific value of the parameter, which is a specific acquisition condition, is within a designated value range into the condition category in which the acquisition conditions are handled as the acquisition condition that is the same as or similar to the specific acquisition condition.

Each of the imaging apparatus and the inspection apparatus is a form of "apparatus used to obtain data". The range of the condition belonging to the condition category handled as the same or a similar condition may be designated in advance or may be dynamically designated according to an instruction from the integration server or the like.

In the machine learning system according to still another aspect of the present disclosure, a combination of conditions in which a plurality of acquisition conditions are handled as a similar condition may be designated, and the learning data classification processing unit may perform the classification into the condition category according to a setting of the designated similar condition.

In the machine learning system according to still another aspect of the present disclosure, each of the plurality of client terminals may be a terminal provided in a medical institution network of a different medical institution.

In the machine learning system according to still another aspect of the present disclosure, the integration server may be provided in a medical institution network or outside the medical institution network.

In the machine learning system according to still another aspect of the present disclosure, the learning results transmitted from the client terminal to the integration server may include a weight parameter of the learning model after the learning.

In the machine learning system according to still another aspect of the present disclosure, the data used as the learning data may include at least one type of data among a two-dimensional image, a three-dimensional image, a moving image, time-series data, or document data.

In the machine learning system according to still another aspect of the present disclosure, each model of the learning model, the master model, and the master model candidate may be configured by using a neural network.

An appropriate network model is applied according to a type of the learning data and a type of data that is input in the inference.

In the machine learning system according to still another aspect of the present disclosure, the data used as the learning data may include a two-dimensional image, a three-dimensional image, or a moving image, and each model of the learning model, the master model, and the master model candidate may be configured by using a convolutional neural network.

In the machine learning system according to still another aspect of the present disclosure, the data used as the learning data may include time-series data or document data, and each model of the learning model, the master model, and the master model candidate may be configured by using a recurrent neural network.

In the machine learning system according to still another aspect of the present disclosure, the integration server may further include an information storage unit that stores information indicating a correspondence relationship as to which client cluster among a plurality of client clusters each of the plurality of master model candidates created is based on.

In the machine learning system according to still another aspect of the present disclosure, the integration server may further include a display device on which information indicating a progress status of learning of each of the master model candidates is displayed.

In the machine learning system according to still another aspect of the present disclosure, a verification data storage unit that stores verification data classified based on a data acquisition condition is further included, and the accuracy evaluation unit may evaluate the inference accuracy of the master model candidate using the verification data.

The verification data storage unit may be included in the integration server or may be an external storage apparatus connected to the integration server.

In the machine learning system according to still another aspect of the present disclosure, the accuracy evaluation unit may include an inference accuracy calculation unit that compares an inference result output from the master model candidate by inputting verification data to the master model candidate with correct answer data of the verification data to calculate the inference accuracy of the master model candidate, and an accuracy target value comparison unit that compares the inference accuracy of the master model candidate with an accuracy target value.

A machine learning method according to still another aspect of the present disclosure uses a plurality of client terminals and an integration server. The machine learning method includes classifying, via each of the plurality of client terminals, data stored in a data storage apparatus of each of different medical institutions based on an acquisition condition of the data to classify learning data into each data group acquired under the same or a similar acquisition condition, synchronizing a learning model of each client terminal side with a trained master model stored in the integration server before each of the plurality of client terminals trains the learning model, executing, via each of the plurality of client terminals, machine learning of the learning model for each learning data group classified into each condition category of the same or a similar acquisition condition, transmitting, via each of the plurality of client terminals, learning results of the learning model executed for each learning data group and condition information regarding the acquisition condition of the learning data group used for the learning, to the integration server, and, via the integration server, receiving the learning results of the learning model and the condition information from each of the plurality of client terminals, classifying the learning results into each condition category, integrating the learning results for each condition category to create a plurality of master model candidates, and evaluating an inference accuracy of each of the plurality of master model candidates.

An integration server according to another aspect of the present disclosure is connected to a plurality of client terminals via a communication line. The integration server includes a master model storage unit that stores a trained master model, a synchronization processing unit that synchronizes a learning model of each client terminal with the master model before each of the plurality of client terminals trains the learning model, a reception unit that receives learning results of the learning model and condition information regarding an acquisition condition of data included in a learning data group used for the learning from each of the plurality of client terminals, a classification processing unit that classifies the learning results into each condition category in which the acquisition condition is handled as the same or a similar condition, a master model candidate creation unit that integrates the learning results for each condition category to create a plurality of master model candidates, and an accuracy evaluation unit that evaluates an inference accuracy of each of the plurality of master model candidates.

The integration server according to another aspect of the present disclosure is connected to a plurality of client terminals via a communication line. The integration server includes a first processor and a first computer-readable medium, which is a non-transitory tangible medium, on which a first program executed by the first processor is recorded. The first processor executes, according to an instruction of the first program, processing including storing a trained master model on the first computer-readable medium, synchronizing a learning model of each client terminal side with the master model before each of the plurality of client terminals trains the learning model, receiving learning results of the learning model and condition information regarding an acquisition condition of data included in a learning data group used for the learning from each of the plurality of client terminals, classifying the learning results into each condition category in which the acquisition condition is handled as the same or a similar condition, integrating the learning results for each condition category to create a plurality of master model candidates, and evaluating an inference accuracy of each of the plurality of master model candidates.

A program according to still another aspect of the present disclosure is a program for causing a computer to function as an integration server connected to a plurality of client terminals via a communication line. The program causes the computer to realize a function of storing a trained master model, a function of synchronizing a learning model of each client terminal side with the master model before each of the plurality of client terminals trains the learning model, a function of receiving learning results of the learning model and condition information regarding an acquisition condition of data included in a learning data group used for the learning from each of the plurality of client terminals, a function of classifying the learning results into each condition category in which the acquisition condition is handled as the same or a similar condition, a function of integrating the learning results for each condition category to create a plurality of master model candidates, and a function of evaluating an inference accuracy of each of the plurality of master model candidates.

An information processing apparatus according to another aspect of the present disclosure is used as a client terminal connected to an integration server via a communication line. The information processing apparatus includes a learning data classification processing unit that classifies data stored in a data storage apparatus of a medical institution based on an acquisition condition of the data to classify learning data into each data group acquired under the same or a similar acquisition condition, a learning processing unit that executes, with a learning model synchronized with a master model stored in the integration server as the learning model in an initial state before learning starts, machine learning of the learning model for each learning data group classified by the learning data classification processing unit into each condition category of the same or a similar acquisition condition, and a transmission unit that transmits learning results of the learning model executed for each learning data group and condition information regarding the acquisition condition of the learning data group used for the learning, to the integration server.

An information processing apparatus according to another aspect of the present disclosure is used as a client terminal connected to an integration server via a communication line. The information processing apparatus includes a second processor and a second computer-readable medium, which is a non-transitory tangible medium, on which a second program executed by the second processor is recorded. The second processor executes, according to an instruction of the second program, processing including classifying data stored in a data storage apparatus of a medical institution based on an acquisition condition of the data to classify learning data into each data group acquired under the same or a similar acquisition condition, executing, with a learning model synchronized with a master model stored in the integration server as the learning model in an initial state before learning starts, machine learning of the learning model for each learning data group classified into each condition category of the same or a similar acquisition condition, and transmitting learning results of the learning model executed for each learning data group and condition information regarding the acquisition condition of the learning data group used for the learning, to the integration server.

A program according to another aspect of the present disclosure is a program for causing a computer to function as a client terminal connected to an integration server via a communication line. The program causes the computer to realize a function of classifying data stored in a data storage apparatus of a medical institution based on an acquisition condition of the data to classify learning data into each data group acquired under the same or a similar acquisition condition, a function of executing, with a learning model synchronized with a master model stored in the integration server as the learning model in an initial state before learning starts, machine learning of the learning model for each learning data group classified into each condition category of the same or a similar acquisition condition, and a function of transmitting learning results of the learning model executed for each learning data group and condition information regarding the acquisition condition of the learning data group used for the learning, to the integration server.

A method of creating an inference model according to still another aspect of the present disclosure is an inference model creation method by performing machine learning using a plurality of client terminals and an integration server. The inference model creation method includes classifying, via each of the plurality of client terminals, data stored in a data storage apparatus of each of different medical institutions based on an acquisition condition of the data to classify learning data into each data group acquired under the same or a similar acquisition condition, synchronizing a learning model of each client terminal side with a trained master model stored in the integration server before each of the plurality of client terminals trains the learning model, executing, via each of the plurality of client terminals, machine learning of the learning model for each learning data group classified into each condition category of the same or a similar acquisition condition, transmitting, via each of the plurality of client terminals, learning results of the learning model executed for each learning data group and condition information regarding the acquisition condition of the learning data group used for the learning, to the integration server, and, via the integration server, receiving the learning results of the learning model and the condition information from each of the plurality of client terminals, classifying the learning results into each condition category, integrating the learning results for each condition category to create a plurality of master model candidates, evaluating an inference accuracy of each of the plurality of master model candidates, and creating an inference model with higher inference accuracy than the master model based on a model whose inference accuracy satisfies a target accuracy among the plurality of master model candidates.

The inference model creation method is understood as an invention of a method of producing the inference model. The term "inference" includes concepts of prediction, estimation, classification, and determination. The inference model may be paraphrased as an "AI model".

According to the present invention, it is possible to perform the learning for each learning data group in which the quality of the data used for the learning is substantially homogenized. Accordingly, it is possible to efficiently perform the learning and thus to improve the inference accuracy of the model.

BRIEF DESCRIPTION OF THE DRAWINGS

FIG. 8 is a flowchart illustrating an example of an operation of the integration server based on a master model learning management program.

FIG. 9 is a flowchart illustrating an example of processing of evaluating an inference accuracy of a master model candidate in the integration server.

FIG. 10 is a block diagram illustrating an example of a hardware configuration of a computer.

DESCRIPTION OF THE PREFERRED EMBODIMENTS

Hereinafter, preferred embodiments of the present invention will be described with reference to the accompanying drawings.

<<Outline of Machine Learning System>>

Figure 1:
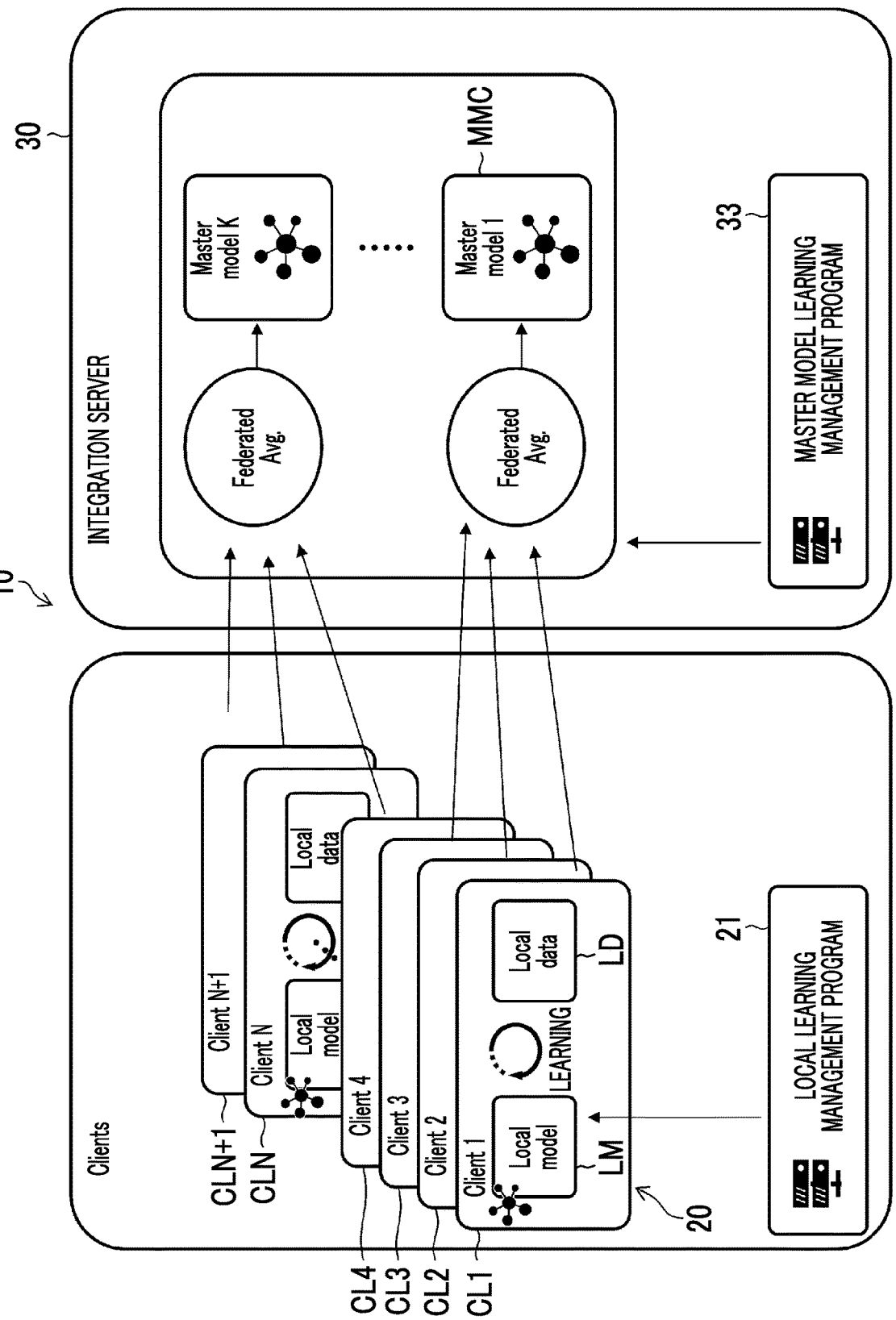
FIG. 1 is a conceptual diagram illustrating an outline of a machine learning system according to an embodiment of the present invention.

FIG. 1 is a conceptual diagram illustrating an outline of a machine learning system according to an embodiment of the present invention. A machine learning system 10 is a computer system that performs machine learning using a federated learning mechanism. The machine learning system 10 includes a plurality of clients 20 and an integration server 30. Federated learning is sometimes referred to as "federation learning", "cooperative learning", or "combination learning".

Each of the plurality of clients 20 illustrated in FIG. 1 indicates a medical institution terminal that is provided on a network in a medical institution such as a hospital. Here, the term "terminal" refers to a computing resource existing in a network that can safely access data in a medical institution, and the terminal may not physically exist in the medical institution. That is, the client 20 may be a physical machine or a virtual machine, and the specific form thereof is not limited. The client 20 is an example of a "client terminal" according to the present disclosure. A computer network in a medical institution is referred to as a "medical institution network".

It is assumed that each client 20 exists for each data group for training an AI model. The term "for each data group" described herein may be understood as "for each medical institution" that holds a data group to be used for the training of the AI model. That is, it is assumed that one client exists for one medical institution.

In order to distinguish and display each of the plurality of clients 20, representations such as "Client 1" and "Client 2" are used in FIG. 1 and subsequent drawings. A number after "Client" is an index as an identification number for identifying each client 20. In the present specification, the client 20 having an index of m is represented by a "client CLm". For example, the client CL1 represents "Client 1" in FIG. 1. m corresponds to a client identification number (ID number). Assuming that a total number of the clients 20 managed by the integration server 30 is M, m represents an integer equal to or larger than 1 and equal to or smaller than M. In FIG. 1, the clients 20 having indexes from m=1 to m=N+1 are illustrated. N represents an integer equal to or larger than 2. An entire set of the clients 20 having a total number of M and participating in the learning is referred to as a "learning client group" or a "client population".

Each client 20 holds local data LD in a storage apparatus of a local client. The local data LD is a data group accumulated by a medical institution to which the client 20 belongs.

Each client 20 includes a local learning management program 21, which is a distribution learning client program. Each client 20 performs an iteration for the training of a local model LM using the local data LD of the local client according to the local learning management program 21.

The local learning management program 21 is a program installed in each client 20. The local learning management program 21 classifies image groups for each similar imaging condition in the client 20 or manages synchronization between the local model LM and a master model on the integration server 30.

Here, the term "imaging condition" may be all or some of imaging parameters that can be set at the time of imaging, such as a type of apparatus in use, a model number of an imaging apparatus used for imaging and a radiation dose.

The term "for each similar imaging condition" means for each imaging condition group in a case where one or a plurality of conditions that fall into a category of similar imaging conditions are collectively defined as the same imaging condition group. The term "group" can be rephrased as a term such as "category", "type", "class", "group", or "classification division". The category of similar imaging conditions can be designated as appropriate according to a type of data to be targeted and/or a task of inference.

In the present specification, a unit of classification of the imaging condition group, which is collected as similar imaging conditions, is referred to as an "imaging condition category". The description "for each similar imaging condition" is synonymous with the description "for each imaging condition category" or "for each identical imaging condition". The imaging condition category may be defined as a specific imaging condition that does not include a similar range. The imaging condition category is an example of the "condition category" in the present disclosure.

The local learning management program 21 classifies the local data LD for each imaging condition category. Further, the local learning management program 21 creates the local model LM for each data group of the classified local data LD and performs the training of the corresponding local model LM by using the classified local data LD.

The local model LM is, for example, an AI model for medical image diagnosis that is incorporated in a CAD system. The term "CAD" includes concepts of both computer aided detection (CADe) and computer aided diagnosis (CADx). The local model LM is configured using, for example, a hierarchical multi-layer neural network. In the local model LM, a network weight parameter is updated by deep learning using the local data LD as learning data. The weight parameter includes a filter coefficient (weight of a connection between nodes) of a filter used for processing of each layer and a bias of a node. The local model LM is an example of a "learning model of client terminal side" according to the present disclosure.

The term "neural network" is a mathematical model for information processing that simulates a mechanism of a brain-nervous system. Processing using the neural network can be realized by using a computer. A processing unit including the neural network may be configured as a program module.

As a network structure of the neural network used for the learning, an appropriate network structure is employed according to a type of data used for input. The AI model for medical image diagnosis may be configured using, for example, various convolutional neural networks (CNNs) having a convolutional layer. The AI model that handles time-series data, document data, or the like may be configured using, for example, various recurrent neural networks (RNNs).

The plurality of clients 20 are connected to the integration server 30 via a communication network. The client 20 transmits a learning result of each local model LM and imaging condition information of the data used for the learning to the integration server 30. The imaging condition information may be information representing the imaging condition category, information indicating actual imaging conditions, or a combination of the pieces of information. The imaging condition information is an example of "condition information" in the present disclosure.

The integration server 30 receives each learning result and the imaging condition information from the plurality of clients 20, classifies the learning results for each imaging condition category, and integrates the learning results for each imaging condition category to create a plurality of master model candidates MMC. Further, the integration server 30 performs processing of evaluating an inference accuracy of each created master model candidate MMC.

A location of the integration server 30 may be on a computer network on which an entity developing the AI model has access rights, and a form of the server may be a physical server, a virtual server, or the like. The integration server 30 may be provided in a medical institution network, or may be provided outside a medical institution network. For example, the integration server 30 may be provided in a company that is located geographically away from a medical institution and that develops medical AI or may be provided on a cloud.

The integration server 30 includes a master model learning management program 33. The master model learning management program 33 classifies and collects the learning results transmitted from the client 20 for each similar imaging condition (imaging condition category) and creates the master model candidate MMC for each imaging condition category. Collectively grouping the learning results for each imaging condition category is equivalent to grouping the clients 20, which are the transmission sources of the learning results, for each imaging condition category to create a client cluster. The client cluster is a part of the client group extracted from the client population. In the present specification, the client group which is a combination of the clients 20 used to create the master model candidate MMC is referred to as "client cluster".

Here, K types of imaging condition categories are assumed to be set. K is an integer equal to or larger than 2. The integration server 30 creates K groups of the client clusters from the client population and creates K master model candidates MMC by integrating the learning results for each client cluster. One client 20 may be an element of a plurality of client clusters. The number of clients 20 (the number of clients) constituting each of the K groups of the client clusters is preferably the same, but may be different.

In FIG. 1, the clients CL1, CL2, and CL3 belong to the same client cluster, and the clients CL4, CLN, and CLN+1 belong to the same client cluster.

In FIG. 1, an arrow extending from a left side of a circle surrounding a display "Federated Avg" indicates that data of the trained local model LM is transmitted from each client 20 belonging to the same client cluster. The data of the local model LM as a learning result provided from each client 20 to the integration server 30 may be the weight parameter of the trained local model LM.

The circle surrounding the display "Federated Avg" represents processing of integrating the learning results. In the processing, the weights transmitted from each client 20 are integrated by averaging or the like to create the master model candidate MMC, which is an integration model. A method of integration processing is not limited to a simple arithmetic mean. The integration may be performed with the weights based on factors such as an attribute of the client 20, a past integration result, the number of pieces of data for each medical institution used for re-learning, and a level of a medical institution evaluated by people.

In FIG. 1, "Master model 1" and "Master model K" illustrated at ends of arrows extending to a right side of the circle surrounding the display "Federated Avg" indicate the master model candidates MMC created from each client cluster. Assuming that an index for identifying each of the K groups of the client clusters is k, k represents an integer equal to or larger than 1 and equal to or smaller than K. The index "k" may be understood as an index that identifies the K types of imaging condition categories. In the present specification, the master model candidate MMC created by integrating the learning results of each client 20 belonging to the client cluster having the index k may be represented as "MMCk". For example, the master model candidate MMC1 represents "Master model 1" in FIG. 1.

The master model learning management program 33 of the integration server 30 evaluates the inference accuracy of the master model candidate MMC using verification data for each of various imaging condition categories prepared in advance. The verification data for each of the various imaging condition categories may be stored in an internal storage apparatus of the integration server 30 or may be stored in an external storage apparatus connected to the integration server 30.

The integration server 30 repeats the learning in the client 20 and the training of the master model candidate MMC for each identical imaging condition until each master model candidate MMC achieves a desired inference accuracy.

Figure 2:
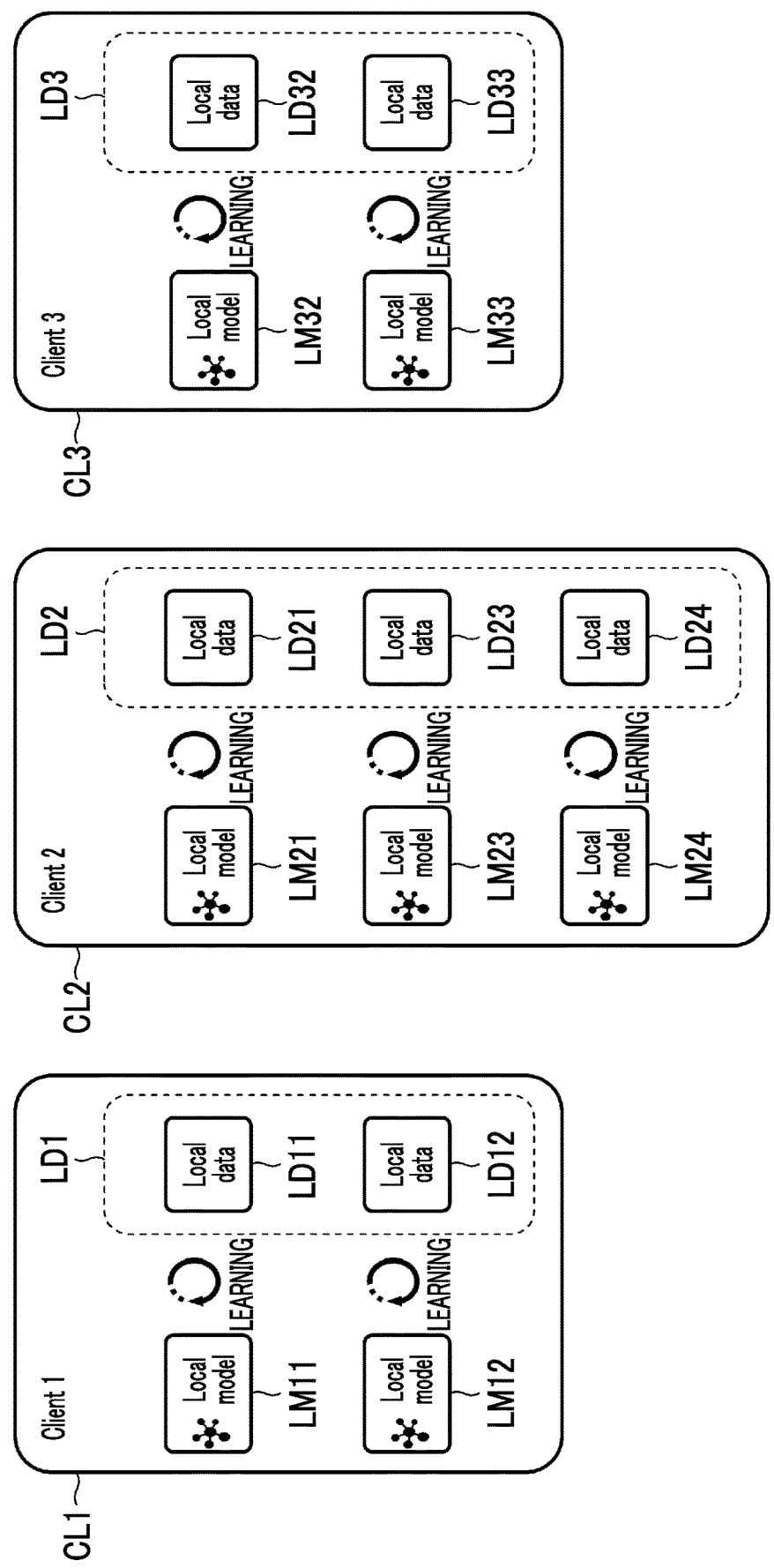
FIG. 2 is a conceptual diagram illustrating an example of local learning performed for each client.

FIG. 2 is a conceptual diagram illustrating an example of local learning performed for each client 20. FIG. 2 shows an example of the local learning performed in the clients CL1, CL2, and CL3. In FIG. 2, the representation of local data LDm represents local data held by the medical institution to which the client CLm specified by the index m belongs. The representation of local data LDmk is data collected by classifying the local data LDm for each similar imaging condition and represents the local data of the imaging condition category specified by the index k. The representation of a local model LMmk represents a local model on which the learning using the local data LDmk is performed in the client CLm.

The local data LD1 of the client CL1 shown in FIG. 2 is classified into each similar imaging condition. For example, the local data LD1 of the client CL1 is divided into local data LD11 including an image group imaged under imaging conditions belonging to a first imaging condition category and local data LD12 including an image group imaged under imaging conditions belonging to a second imaging condition category.

The client CL1 performs the training of a local model LM11 using the local data LD11 as the learning data and performs the training of a local model LM12 using the local data LD12 as the learning data.

The local data LD2 of the client CL2 shown in FIG. 2 includes, for example, local data LD21 including an image group imaged under imaging conditions belonging to the first imaging condition category, local data LD23 including an image group imaged under imaging conditions belonging to a third imaging condition category, and local data LD24 including an image group imaged under imaging conditions belonging to a fourth imaging condition category. The client CL2 performs the training of a local model LM21 using the local data LD21 as the learning data, performs the training of a local model LM23 using the local data LD23 as the learning data, and performs the training of a local model LM24 using the local data LD24 as the learning data.

The local data LD3 of the client CL3 shown in FIG. 2 is divided into, for example, local data LD32 including an image group imaged under imaging conditions belonging to the second imaging condition category and local data LD33 including an image group imaged under imaging conditions belonging to the third imaging condition category. The client CL3 performs the training of a local model LM32 using the local data LD32 as the learning data and performs the training of a local model LM33 using the local data LD33 as the learning data.

The number of local models LMmk to be trained in each client CLm is not limited to the example of FIG. 2 and may have various forms depending on contents of the local data LDm. In a case where the local data LDm of the client CLm includes the local data LDmk of a k-th imaging condition category, the client CLm can perform the training of the local model LMmk using the local data LDmk as the learning data. Each client CLm can perform the training of one or more local models LMmk. The local data LDmk is an example of the "data group acquired under the same or a similar acquisition condition" and the "learning data group classified into each condition category" in the present disclosure.

Figure 3:
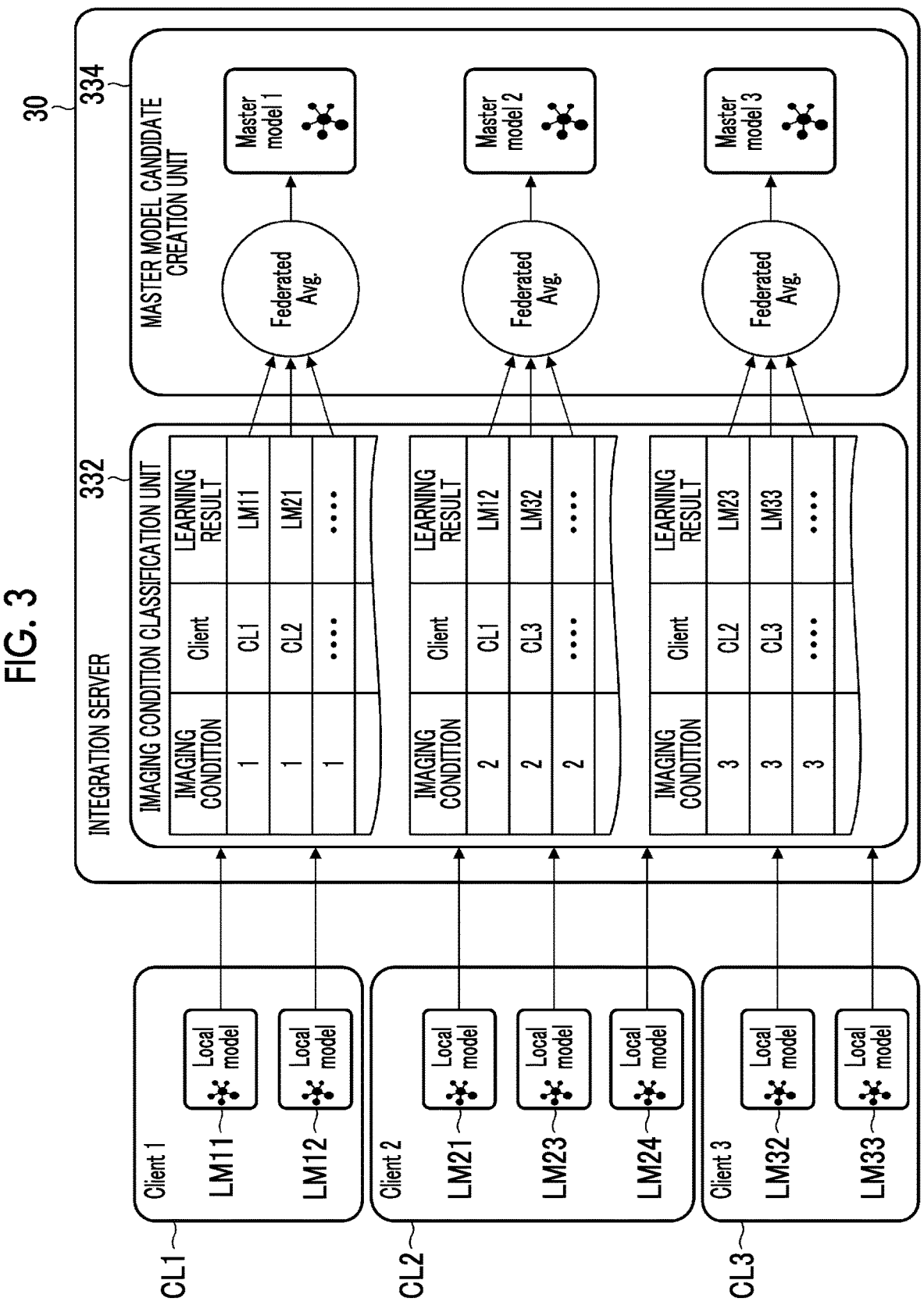
FIG. 3 is a conceptual diagram illustrating an example of creation processing of a master model candidate performed on an integration server.

FIG. 3 is a conceptual diagram illustrating an example of creation processing of the master model candidate MMC performed on the integration server 30. FIG. 3 illustrates a state where the learning results and the imaging condition information are transmitted from the clients CL1, CL2, and CL3 illustrated in FIG. 2 to the integration server 30.

The integration server 30 includes an imaging condition classification unit 332 and a master model candidate creation unit 334. The imaging condition classification unit 332 classifies the learning result data transmitted from the client CLm for each imaging condition category to create the client cluster for each imaging condition category. A table displayed in a frame of the imaging condition classification unit 332 in FIG. 3 conceptually illustrates a collection of classified and organized data. Numbers "1", "2", and "3" in a column displayed as "imaging condition" in the same table indicate values of index "k" of the imaging condition category. A collection of the clients CLm displayed in cells of a column displayed as "Client" corresponds to the client cluster. The imaging condition classification unit 332 is an example of a "classification processing unit" in the present disclosure.

The master model candidate creation unit 334 integrates the learning results of the client clusters for each imaging condition category classified by the imaging condition classification unit 332 to create a master model candidate MMCk. That is, the master model candidate creation unit 334 creates the master model candidate MMCk using the learning results classified into the k-th imaging condition category.

<<Outline of Machine Learning Method>>

An example of a machine learning method by the machine learning system 10 according to the embodiment of the present invention will be described. The machine learning system 10 operates according to procedure 1 to procedure 11 described below.

[Procedure 1] As illustrated in FIG. 1, the distribution learning client program for federated learning is executed on the medical institution terminal (client 20) that is provided on the computer network of the medical institution in which the data group for training the AI model exists.

[Procedure 2] In each medical institution network, the image used for the learning is stored together with the imaging condition in a place accessible from the local learning management program 21.

[Procedure 3] The local learning management program 21 of the client 20 determines whether or not the local model LM exists on the terminal of the client 20. In a case where the local model LM does not exist, the required number of learning images is collected and classified into each similar imaging condition from the local data LD. In a similar classification handled as "similar imaging condition" in this case, imaging conditions in which a specific imaging condition (for example, specific radiation dose) according to the purpose of learning is within a designated value range may be classified into the same condition division (imaging condition category) as "similar imaging condition", or conditions in which a plurality of different imaging conditions are handled as a similar condition may be set, and imaging conditions according to the setting may be classified into the same condition division as "similar imaging condition". The radiation dose is an example of "imaging parameter that can be set at the time of imaging" and "parameter that can be set in the apparatus used to obtain data" in the present disclosure. A value of the radiation dose is an example of "imaging parameter value" and "parameter value" in the present disclosure.

On the other hand, a case where the local model LM already exists means that the image classification for each similar imaging condition has already been performed. Therefore, there may be no need to newly create the learning data group for each imaging condition category for the learning.

[Procedure 4] The integration server 30 synchronizes, in a case where the latest version of the master model for the learning exists, the latest version of the master model with the local model LM on each client 20 before each of the plurality of clients 20 starts the learning. The master model is a trained AI model. In this case, a relationship between the local model LM and the master model, which are synchronized, is maintained in the subsequent learning process.

[Procedure 5] In the client 20, the local model LM is created for each imaging condition category created in procedure 3 according to the local learning management program 21, and the training of each local model LM proceeds for each imaging condition category. In this case, the training of each local model LM may proceed by the designated number of iterations or may proceed until designated accuracy improvement is satisfied with the designated upper limit number of iterations as an upper limit. Here, the learning "for each imaging condition category" means that conditions of the data (learning data) used for the learning are closer to uniform than those of random extraction, and thus it is expected that the learning is effectively performed by the homogenization of the learning data.

[Procedure 6] The client 20 transmits, in a case where the training of the local model LM ends, the learning result of the local model LM to the integration server 30 in association with the imaging conditions of the data group used for the learning. The learning result transmitted from the client 20 to the integration server 30 may be the weight parameter of the trained local model LM. The data of the weight parameter after learning that is transmitted from the client 20 to the integration server 30 may be a difference from the weight parameter of the latest version of the master model synchronized with the integration server 30.

[Procedure 7] The integration server 30 stores the learning result transmitted from each client 20 and metadata such as the imaging condition accompanying the learning result in a data storage unit such as a database.

[Procedure 8] The master model learning management program 33 on the integration server 30 creates the classification of similar imaging conditions based on the learning result of the client 20 and the metadata accompanying the learning result which are stored in procedure 7. Further, the master model learning management program 33 creates the client cluster for each of the classified similar imaging conditions (for each imaging condition category) and creates the master model candidate MMC from each of the client clusters. Accordingly, the plurality of master model candidate MMCs are created. The master model learning management program 33 stores a correspondence relationship as to from which client cluster each master model candidate MMC is created in the data storage unit such as the database. The relationship (correspondence relationship) between the client cluster and the master model candidate MMC is maintained until the subsequent training of the master model candidate MMC ends.

[Procedure 9] The master model learning management program 33 evaluates the inference accuracy for each master model candidate MMC, using the verification data for each imaging condition prepared in advance on the integration server 30 or in an environment where the integration server 30 has access. That is, the master model learning management program 33 causes the master model candidate MMC to perform an inference by using the verification data as an input to the master model candidate MMC, compares an inference result with correct answer data to calculate the inference accuracy, and stores the inference accuracy of the master model candidate MMC in the data storage unit such as the database.

[Procedure 10] In a case where the inference accuracy of the master model candidate MMC exceeds a target accuracy as a result of measuring the accuracy of the master model candidate MMC in procedure 9, the master model learning management program 33 ends the training of the master model candidate MMC and sends notification of the end of the learning thereof.

[Procedure 11] In a case where the inference accuracy of the master model candidate MMC does not reach the target accuracy as a result of measuring the accuracy of the master model candidate MMC in procedure 9, the local model LM of the client cluster used to create the master model candidate MMC is synchronized with the master model candidate MMC using the information stored in procedure 8, and the procedures 5 to 11 are repeated. In the synchronization processing of procedure 11, the master model candidate MMC having the highest inference accuracy among the plurality of master model candidate MMCs may be synchronized with the local model LM.

Accordingly, it is possible to create the master model candidate MMC by integrating the learning results with the image group acquired under substantially uniform imaging conditions for each imaging condition category as the learning data. According to the present embodiment, with the homogenization of the imaging conditions of the learning data, it is possible to efficiently perform the learning and to improve the inference accuracy of the model. With the implementation of the machine learning method using the machine learning system 10 according to the present embodiment, it is possible to create an inference model having an inference accuracy that satisfies the target accuracy. The machine learning method using the machine learning system 10 according to the present embodiment is understood as an inference model creation method.

<<System Configuration Example>>

Figure 4:
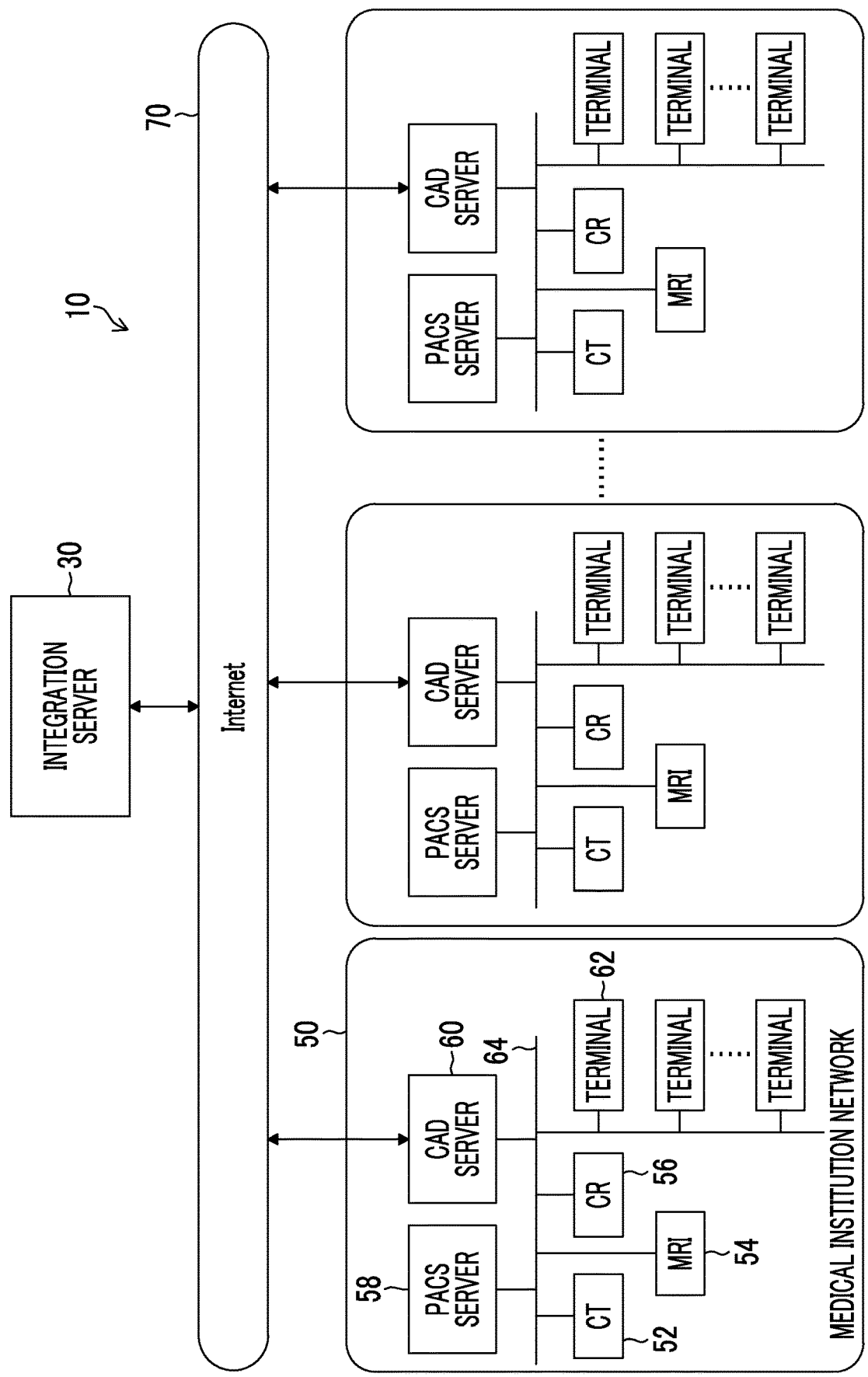
FIG. 4 is a diagram schematically illustrating a system configuration example of the machine learning system according to the embodiment of the present invention.

Next, an example of a specific configuration of the machine learning system 10 will be described. FIG. 4 is a diagram schematically illustrating a system configuration example of the machine learning system 10 according to the embodiment of the present invention. First, an example of a medical institution network 50 will be described. For simplicity of illustration, FIG. 4 illustrates an example in which the medical institution network 50 having the same system configuration is provided in each of a plurality of medical institutions. However, a medical institution network having a different system configuration for each medical institution may be provided.

The medical institution network 50 is a computer network including a computed tomography (CT) apparatus 52, a magnetic resonance imaging (MM) apparatus 54, a computed radiography (CR) apparatus 56, a picture archiving and communication systems (PACS) server 58, a CAD server 60, a terminal 62, and an internal communication line 64.

The medical institution network 50 is not limited to the CT apparatus 52, the MM apparatus 54, and the CR apparatus 56 illustrated in FIG. 4. Instead of some or all of the apparatuses or in addition to the apparatuses, the medical institution network 50 may include at least one or a combination of a digital X-ray imaging apparatus, an angiography X-ray diagnosis apparatus, an ultrasound diagnostic apparatus, a positron emission tomography (PET) apparatus, an endoscopic apparatus, a mammography apparatus, and various inspection apparatuses (modalities) which are not illustrated. There may be various combinations of types of inspection apparatuses connected to the medical institution network 50 for each medical institution. Each of the CT apparatus 52, the MRI apparatus 54, and the CR apparatus 56 is an example of the "imaging apparatus" in the present disclosure.

The PACS server 58 is a computer that stores and manages various data and comprises a large-capacity external storage apparatus and database management software. The PACS server 58 performs a communication with another apparatus via the internal communication line 64, and transmits and receives various data including image data. The PACS server 58 receives various data including image data and the like generated by each inspection apparatus such as the CT apparatus 52, the MRI apparatus 54, and the CR apparatus 56 via the internal communication line 64, and stores and manages the data in a recording medium such as a large-capacity external storage apparatus.

A storage format of the image data and a communication between the apparatuses via the internal communication line 64 are based on a protocol such as digital imaging and communication in medicine (DICOM). The PACS server 58 may be a DICOM server that operates according to a DICOM specification. The data stored in the PACS server 58 can be used as learning data. The learning data created based on the data stored in the PACS server 58 may be stored in the CAD server 60. The PACS server 58 is an example of a "data storage apparatus of a medical institution" according to the present disclosure. Further, the CAD server 60 may function as the "data storage apparatus of a medical institution" according to the present disclosure.

The CAD server 60 corresponds to the client 20 described in FIG. 1. The CAD server 60 has a communication function for a communication with the integration server 30 and is connected to the integration server 30 via a wide area communication line 70. The CAD server 60 can acquire data from the PACS server 58 or the like via the internal communication line 64. The CAD server 60 includes a local learning management program for executing training of the local model LM on the CAD server 60 using the data group stored in the PACS server 58. The CAD server 60 is an example of a "client terminal" according to the present disclosure.

Various data stored in the database of the PACS server 58 and various information including the inference result by the CAD server 60 can be displayed on the terminal 62 connected to the internal communication line 64.

The terminal 62 may be a display terminal called a PACS viewer or a DICOM viewer. A plurality of terminals 62 may be connected to the medical institution network 50. A form of the terminal 62 is not particularly limited and may be a personal computer, a workstation, a tablet terminal, or the like.

As illustrated in FIG. 4, the medical institution network having the same system configuration is provided in each of the plurality of medical institutions. The integration server 30 performs a communication with a plurality of CAD servers 60 via the wide area communication line 70. The wide area communication line 70 is an example of a "communication line" according to the present disclosure.

<<Configuration Example of Integration Server 30>>

Figure 5:
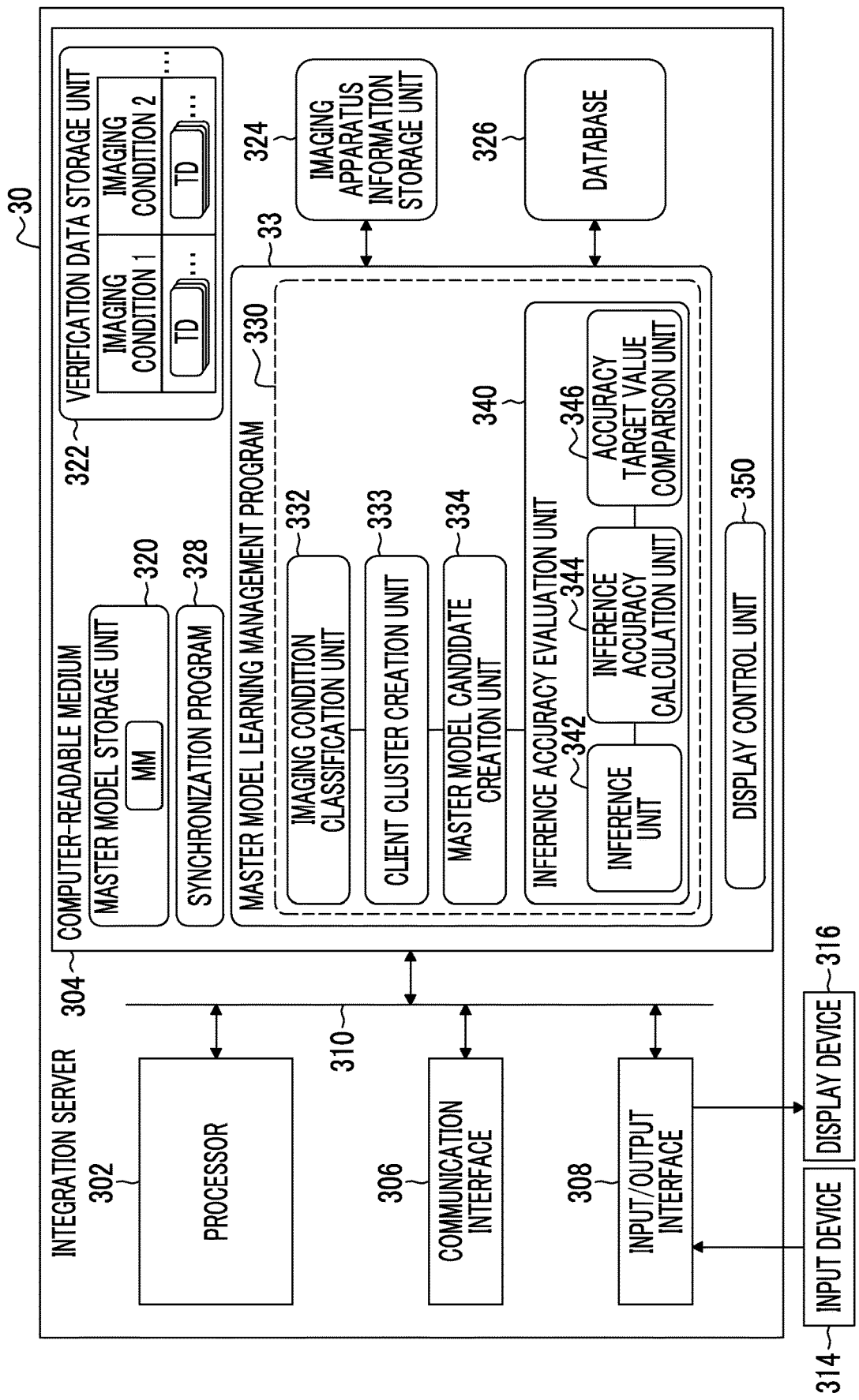
FIG. 5 is a block diagram illustrating a configuration example of an integration server.

FIG. 5 is a block diagram illustrating a configuration example of the integration server 30. The integration server 30 can be formed by a computer system configured by using one or a plurality of computers. The integration server 30 is formed by installing a program on a computer.

The integration server 30 comprises a processor 302, a non-transitory tangible computer-readable medium 304, a communication interface 306, an input/output interface 308, a bus 310, an input device 314, and a display device 316. The processor 302 is an example of a "first processor" according to the present disclosure. The computer-readable medium 304 is an example of a "first computer-readable medium" according to the present disclosure.

The processor 302 includes a central processing unit (CPU). The processor 302 may include a graphics processing unit (GPU). The processor 302 is connected to the computer-readable medium 304, the communication interface 306, and the input/output interface 308 via the bus 310. The input device 314 and the display device 316 are connected to the bus 310 via the input/output interface 308.

The computer-readable medium 304 includes a memory as a main storage unit and a storage as an auxiliary storage device. The computer-readable medium 304 may be, for example, a semiconductor memory, a hard disk drive (HDD) device, a solid state drive (SSD) device, or a combination of these devices.

The integration server 30 is connected to the wide area communication line 70 (refer to FIG. 4) via the communication interface 306.

The computer-readable medium 304 includes a master model storage unit 320, a verification data storage unit 322, an imaging apparatus information storage unit 324, and a database 326. The master model storage unit 320 stores data of the latest version of a master model MM. The verification data storage unit 322 stores a plurality of pieces of verification data TD which are used when verifying the inference accuracy of the integration model created by the master model candidate creation unit 334. The verification data TD is data in which input data and correct answer data are combined, and is also called test data. The verification data TD may be, for example, data provided by a university and the like. The verification data storage unit 322 stores the verification data TD prepared for each imaging condition. The representations "imaging condition 1" and "imaging condition 2" in FIG. 5 represent the imaging condition category, and the number at the end corresponds to the index "k".

The imaging apparatus information storage unit 324 stores imaging apparatus information of the learning client group. The imaging apparatus information includes a manufacturer name and model number of the apparatus which is the imaging apparatus.

The computer-readable medium 304 stores various programs including a synchronization program 328 and the master model learning management program 33, and data. The synchronization program 328 is a program for providing the data of the master model MM to each client 20 via the communication interface 306 and synchronizing each local model LM with the master model MM. In a case where the processor 302 executes an instruction of the synchronization program 328, the computer functions as a synchronization processing unit. The synchronization program 328 may be incorporated as the program module of the master model learning management program 33.

In a case where the processor 302 executes an instruction of the master model learning management program 33, the computer functions as a master model learning management unit 330. The master model learning management unit 330 includes the imaging condition classification unit 332, a client cluster creation unit 333, the master model candidate creation unit 334, and an inference accuracy evaluation unit 340. The inference accuracy evaluation unit 340 includes an inference unit 342, an inference accuracy calculation unit 344, and an accuracy target value comparison unit 346.

The client cluster creation unit 333 creates the client cluster which is the combination of the clients 20 used to create the master model candidate MMC for each imaging condition category classified by the imaging condition classification unit 332. In a case where the client cluster creation unit 333 creates the plurality of client clusters, there is no need to distribute all the clients of the client population to one of the client clusters, and the learning results of some clients 20 may not be used in the integration processing.

The creation of the client cluster by the client cluster creation unit 333 may be performed before each client 20 starts learning, or may be performed after learning is started. For example, the creation of the client cluster may be performed after each learning result is received from each client 20. The communication interface 306 is an example of a "reception unit" according to the present disclosure.

The client cluster creation unit 333 stores, in the database 326, information indicating a correspondence relationship between the information of the clients 20 belonging to each client cluster and the master model candidate MMC created for each client cluster. The database 326 is an example of an "information storage unit" according to the present disclosure.

The master model candidate creation unit 334 creates a master model candidate MMC by integrating the learning results for each client cluster. Information indicating a correspondence relationship as to which client cluster each master model candidate MMC created is based on is stored in the database 326.

The inference accuracy evaluation unit 340 verifies and evaluates the inference accuracy of the master model candidate MMC created for each client cluster.

The inference unit 342 executes an inference by the master model candidate MMC by inputting the verification data TD to the master model candidate MMC. The inference accuracy calculation unit 344 calculates an inference accuracy of the master model candidate MMC by comparing the inference result of the master model candidate MMC obtained from the inference unit 342 with the correct answer data. For example, as the correct answer data, data in which the number of lesions and correct clinical findings are added to the image data is used. The inference accuracy calculation unit 344 performs an accuracy verification a plurality of times through comparison with the verification data TD. The inference accuracy calculation unit 344 may calculate an accuracy average value of the master model candidate MMC from the result obtained by performing the accuracy verification a plurality of times, and evaluate the accuracy average value as the inference accuracy of the master model candidate MMC. The inference accuracy calculated by the inference accuracy calculation unit 344 is stored in the database 326.

The accuracy target value comparison unit 346 selects the inference accuracy of the model having the highest inference accuracy from the plurality of created master model candidates, and determines whether or not the master model candidate having an inference accuracy higher than the accuracy target value is obtained by comparing the inference accuracy with an accuracy target value. The accuracy target value is a value indicating a target accuracy and is, for example, set to an accuracy higher than the inference accuracy of the latest version of the master model MM and is set to an accuracy having a level for commercialization instead of the master model MM.

The synchronization program 328 and the master model learning management program 33 are examples of a "first program" in the present disclosure.

Further, in a case where the processor 302 executes an instruction of a display control program, the computer functions as a display control unit 350. The display control unit 350 generates a display signal required for a display output to the display device 316 and performs a display control of the display device 316.

The display device 316 is configured with, for example, a liquid crystal display, an organic electro-luminescence (OEL) display, a projector, or an appropriate combination thereof. The input device 314 is configured with, for example, a keyboard, a mouse, a touch panel, another pointing device, a voice input device, or an appropriate combination thereof. The input device 314 receives various inputs from an operator. The display device 316 and the input device 314 may be integrally configured by using a touch panel.

The display device 316 can display the inference accuracy in each learning iteration of each of the plurality of master model candidates MMC. That is, information indicating a learning progress status of each of the plurality of master model candidate MMCs can be displayed on the display device 316, and the information displayed on the display device 316 enables the operator to confirm the learning progress status of each master model candidate MMC.

<<Configuration Example of CAD Server 60>>

Figure 6:
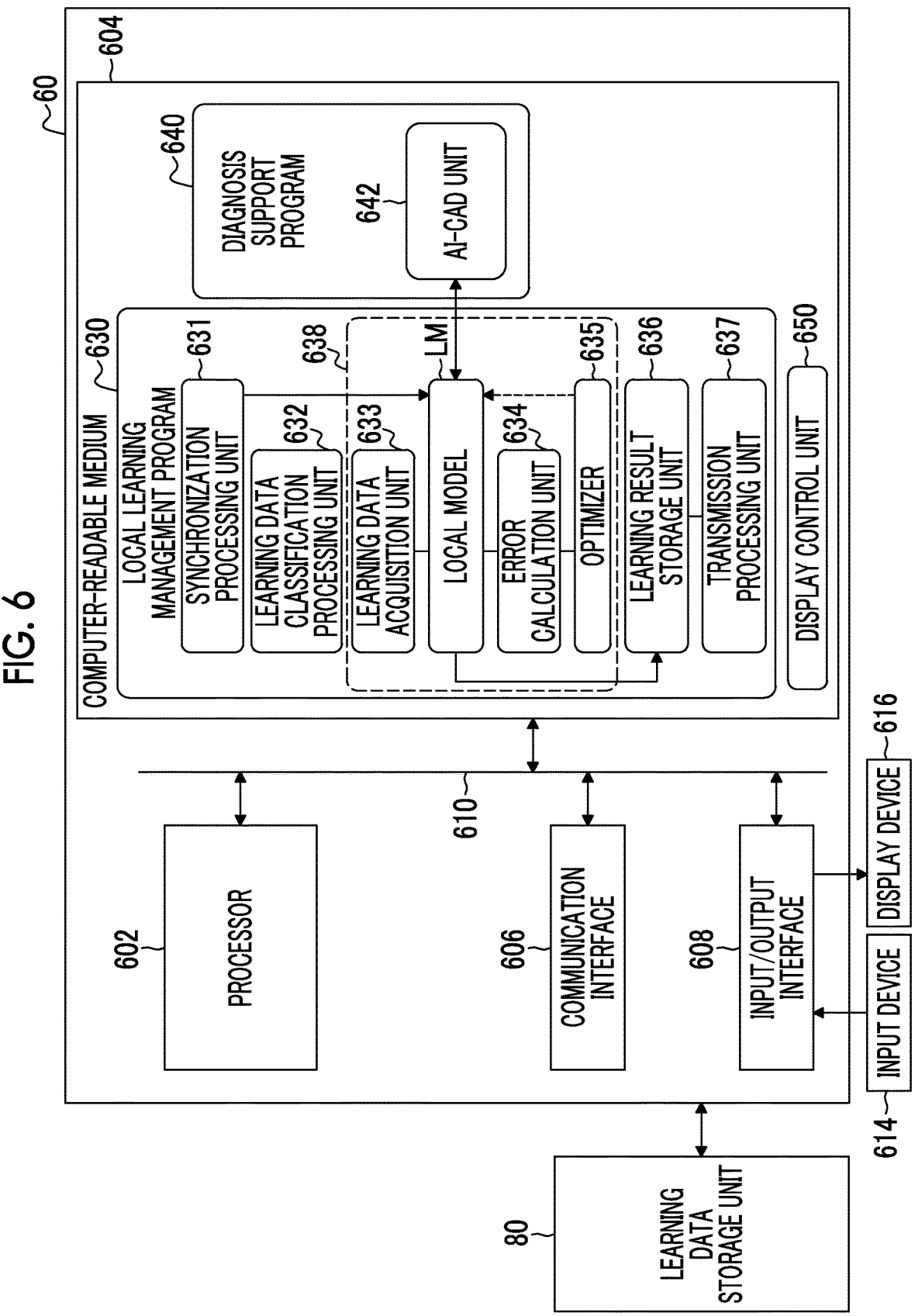
FIG. 6 is a block diagram illustrating a configuration example of a computer aided detection/diagnosis (CAD) server as an example of a client.

FIG. 6 is a block diagram illustrating a configuration example of the CAD server 60 as an example of the client 20. The CAD server 60 can be formed by a computer system configured by using one or a plurality of computers. The CAD server 60 is formed by installing a program on a computer.

The CAD server 60 comprises a processor 602, a non-transitory tangible computer-readable medium 604, a communication interface 606, an input/output interface 608, a bus 610, an input device 614, and a display device 616. The hardware configuration of the CAD server 60 may be the same as the hardware configuration of the integration server 30 described with reference to FIG. 5. That is, the hardware configuration of each of the processor 602, the computer-readable medium 604, the communication interface 606, the input/output interface 608, the bus 610, the input device 614, and the display device 616 in FIG. 6 may be the same as the hardware configuration of each of the processor 302, the computer-readable medium 304, the communication interface 306, the input/output interface 308, the bus 310, the input device 314, and the display device 316 in FIG. 5.

The CAD server 60 is an example of an "information processing apparatus" according to the present disclosure. The processor 602 is an example of a "second processor" according to the present disclosure. The computer-readable medium 604 is an example of a "second computer-readable medium" according to the present disclosure.

The CAD server 60 is connected to a learning data storage unit 80 via the communication interface 606 or the input/output interface 608. The learning data storage unit 80 is configured to include a storage that stores learning data to be used for machine learning by the CAD server 60. The "learning data" is training data used for machine learning and is synonymous with "data for the learning" or "training data". The learning data stored in the learning data storage unit 80 is the local data LD described with reference to FIG. 1. The learning data storage unit 80 may be the PACS server 58 described with reference to FIG. 2. The learning data storage unit 80 is an example of a "data storage apparatus of a medical institution" according to the present disclosure.

Here, an example in which the learning data storage unit 80 and the CAD server 60 that executes learning processing are configured as separate apparatuses will be described. However, the functions may be formed by one computer, or the processing functions may be shared and formed by two or more computers. The computer-readable medium 604 of the CAD server 60 illustrated in FIG. 6 stores various programs, which include a local learning management program 630 and a diagnosis support program 640, and data.

In a case where the processor 602 executes an instruction of the local learning management program 630, the computer functions as a synchronization processing unit 631, a learning data classification processing unit 632, a learning data acquisition unit 633, a local model LM, an error calculation unit 634, an optimizer 635, a learning result storage unit 636, and a transmission processing unit 637. The local learning management program 630 is an example of a "second program" according to the present disclosure.

The synchronization processing unit 631 performs a communication with the integration server 30 via the communication interface 606 and synchronizes the master model MM in the integration server 30 with the local model LM in the CAD server 60.

The learning data classification processing unit 632 classifies the local data LD stored in the learning data storage unit 80 into imaging condition categories and divides the imaging condition categories into a set of learning data for each imaging condition category.

The learning data acquisition unit 633 acquires learning data from the learning data storage unit 80. The learning data acquisition unit 633 may be configured to include a data input terminal for receiving data from an external apparatus or from another signal processing unit in the apparatus. Further, the learning data acquisition unit 633 may be configured to include the communication interface 606, the input/output interface 608, a media interface for performing reading and writing on a portable external storage medium such as a memory card (not illustrated), or an appropriate combination of these interfaces.

The learning data acquired via the learning data acquisition unit 633 is input to the local model LM as a learning model.

The error calculation unit 634 calculates an error between a predicted value indicated by a score which is output from the local model LM and the correct answer data. The error calculation unit 634 evaluates the error using a loss function. The loss function may be, for example, a cross entropy or a mean square error.

The optimizer 635 performs processing of updating a weight parameter of the local model LM from the calculation result of the error calculation unit 634. The optimizer 635 performs calculation processing of obtaining an update amount of the weight parameter of the local model LM and update processing of the weight parameter of the local model LM according to the calculated update amount of the weight parameter, by using the error calculation result obtained from the error calculation unit 634. The optimizer 635 updates the weight parameter based on an algorithm such as a backpropagation.

The learning processing unit 638 including the learning data acquisition unit 633, the local model LM, the error calculation unit 634, and the optimizer 635 may be provided for each imaging condition category classified by the learning data classification processing unit 632.

The CAD server 60 in which the local learning management program 630 is incorporated functions as a local learning apparatus that executes machine learning on the CAD server 60 by using the local data LD as learning data. The CAD server 60 reads the learning data, which is the local data LD, from the learning data storage unit 80 and executes machine learning of each local model LM using the learning data classified into each imaging condition category. The CAD server 60 can update, in a case where the learning data is read in units of mini-batch in which a plurality of pieces of learning data are collected, the weight parameter.

The local learning management program 630 repeats an iteration of the learning processing until a learning end condition is satisfied for each local model LM. After the learning end condition is satisfied, the weight parameter of the local model LM is stored in the learning result storage unit 636 as the learning result.

The transmission processing unit 637 performs processing of transmitting the learning result to the integration server 30. The weight parameter of the trained local model LM stored in the learning result storage unit 636 is transmitted to the integration server 30 via the communication interface 606 and the wide area communication line 70 (refer to FIG. 4). The transmission processing unit 637 and the communication interface 606 are examples of a "transmission unit" according to the present disclosure.

Further, in a case where the processor 602 executes an instruction of the diagnosis support program 640, the computer functions as an AI-CAD unit 642.

The AI-CAD unit 642 outputs an inference result for input data by using, as an inference model, the master model MINI or the local model LM. The input data to the AI-CAD unit 642 is, for example, a medical image such as a two-dimensional image, a three-dimensional image, and a moving image, and an output from the AI-CAD unit 642 is, for example, information indicating a position of a lesion portion in the image, information indicating a class classification such as a disease name, or a combination thereof.

<<Description of Local Learning Management Program 630>>

As described above, the local learning management program 630 is installed on the client terminal (client 20) existing in the medical institution network 50. Here, the client terminal may be, for example, the CAD server 60 in FIG. 4. The local learning management program 630 has a function of synchronizing the master model MINI before performing learning and the local model LM, a function of starting the local learning, a function of setting an end condition of local learning, and a function of transmitting the result of local learning to the integration server 30 when local learning is ended.

Figure 7:
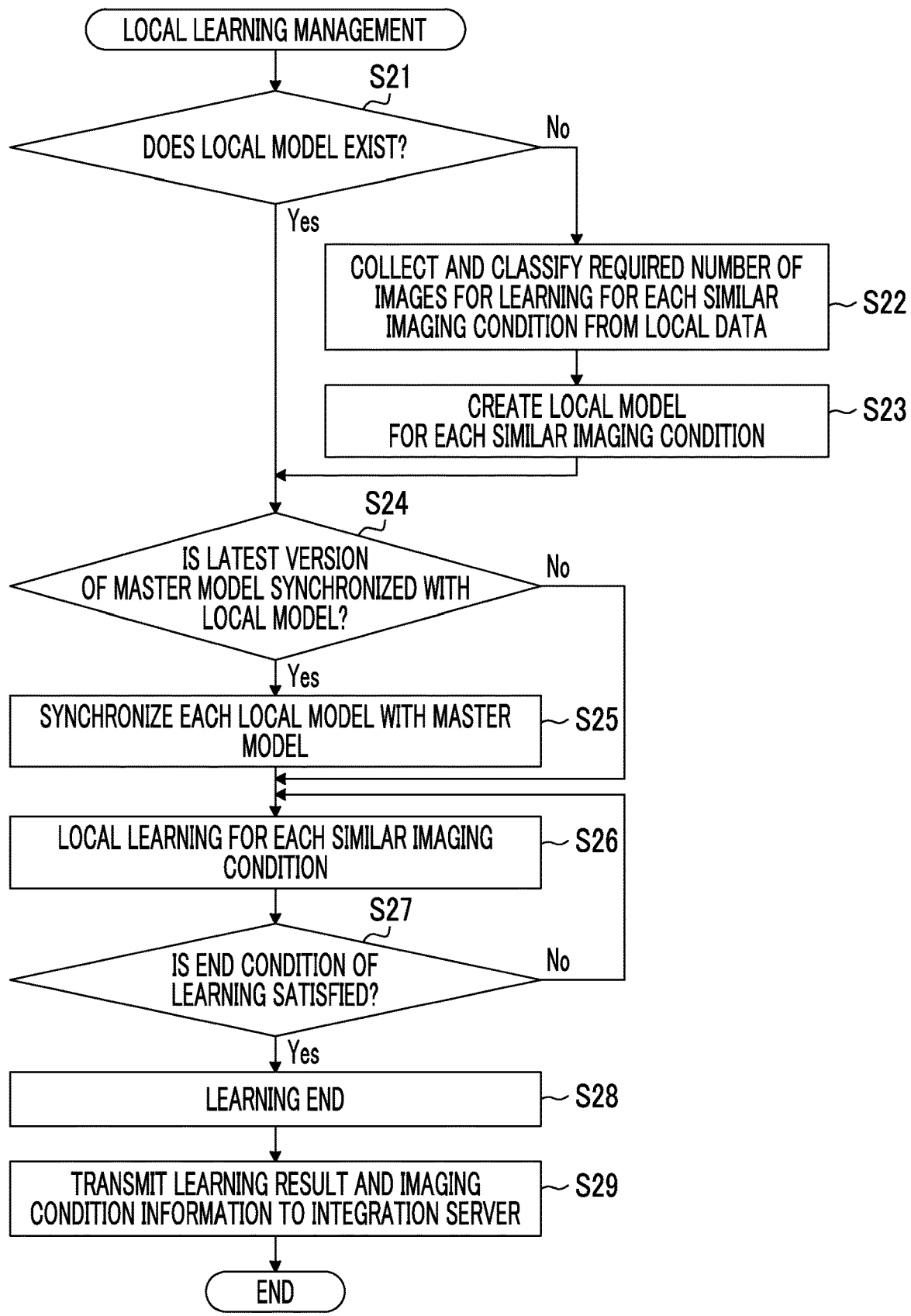
FIG. 7 is a flowchart illustrating an example of an operation of a client terminal based on a local learning management program.

FIG. 7 is a flowchart illustrating an example of an operation of the client terminal based on the local learning management program 630. Steps in the flowchart illustrated in FIG. 7 are executed by the processor 602 according to an instruction of the local learning management program 630.

In step S21, the processor 602 of the CAD server 60 determines whether or not the local model LM created for each imaging condition category exists on the CAD server 60. In a case where a determination result in step S21 is No, the processor 602 proceeds to step S22, collects and classifies the required number of images for the learning for each similar imaging condition from the local data LD, and creates the learning data set for each imaging condition category. In step S23, the processor 602 creates the local model LM for each of the classified similar imaging conditions. After step S23, the processor 602 proceeds to step S24.

On the other hand, in a case where the determination result in step S21 is Yes, that is, in a case where the local model LM already exists, steps S22 and S23 have already been executed, and the image classification for each similar imaging condition is performed. Therefore, the processor 602 proceeds to step S24.

In step S24, the processor 602 determines whether to synchronize the local model LM on the CAD server 60 with the latest version of the master model MM on the integration server 30. The CAD server 60 communicates with the integration server 30 before the learning is started to determine the necessity of the synchronization.

In a case where a determination result in step S24 is Yes, the processor 602 proceeds to step S25 to synchronize each local model LM with the master model MM.

For example, in a case where a new local model LM is created in step S23, the local model LM is synchronized with the master model MM. In a case where the latest version of the master model MM used for the learning exists on the integration server 30, the local model LM is synchronized with the latest version of the master model MM.

In this case, the relationship between the synchronized local model LM and the master model MM, which are synchronized, is maintained in the subsequent learning process. The synchronization method may be a method of downloading and updating a model parameter file of the master model MM on a client side or may be a method of managing a virtual container image or the like of the master model MM on the integration server 30 and downloading the virtual container image or the like to a terminal side, which is the client 20. With the synchronization processing, the master model MINI is a learning model (local model LM) in an initial state before the learning is started.

The processor 602 may synchronize the local model LM with the master model MM, for example, at a point in time set by the local learning management program 630. Here, a "set time" may be designated as a fixed value, for example, a time outside of hospital examination business hours, or may be programmatically set by storing a record of an operating status of the CAD server 60 and determining a time when the CAD server 60 is not normally used.

In a case where the determination is No after step S25 or in step S24, the processor 602 proceeds to step S26.

In step S26, the processor 602 executes the local learning for each similar imaging condition. In the local model LM created for each similar imaging condition, the learning processing of the local model LM is started by the local learning management program 630, and the local learning proceeds using the learning data group for each imaging condition category classified and collected from the local data LD in the medical institution network 50.

In step S27, the processor 602 determines whether or not the learning end condition is satisfied. Here, examples of the learning end condition include the following conditions.

[Example 1] The number of iterations is designated in advance, and learning is ended after the designated number of iterations.

[Example 2] With the upper limit number of iterations as the upper limit, the learning proceeds until the designated accuracy improvement is satisfied. That is, in a state where the verification data TD is stored in the medical institution network 50, the inference accuracy is calculated by performing accuracy comparison between the inference result obtained by inputting the verification data TD into the trained model and the correct answer, and learning is performed until the accuracy improvement of a designated ratio is achieved with the upper limit number of iterations as the upper limit. In a case where the accuracy improvement of the designated ratio is achieved within the upper limit number of iterations set in advance, the learning is ended.

[Example 3] A time limit is set, and the learning is performed within the time limit. In a case where the time limit is reached, the learning is ended.

The end condition of any one of [Example 1] to [Example 3] may be set, or a logical product (AND) or a logical sum (OR) of the plurality of conditions may be set as the end condition.

In a case where a determination result in step S27 is No, the processor 602 returns to step S26 to continue the local learning processing. On the other hand, in a case where the determination result in step S27 is Yes, the processor 602 proceeds to step S28 to end the learning.

After the learning is ended, the processor 602 transmits the learning result of the local model LM and the imaging condition information used for the learning to the integration server 30 in step S29. For example, the processor 602 stores the weight parameter of the trained model in a file and transmits the weight parameter thereof together with the metadata including the imaging condition information to the integration server 30 via the wide area communication line 70.

Each of the plurality of the CAD servers 60 illustrated in FIG. 4 executes machine learning of each local model LM by using, as learning data, data stored in the PACS server 58 in different medical institution networks, and transmits a learning result to the integration server 30 via the wide area communication line 70.

<<Description of Master Model Learning Management Program 33>>

FIG. 8 is a flowchart illustrating an example of an operation of the integration server 30 based on the master model learning management program 33. Steps in the flowchart illustrated in FIG. 8 are executed by the processor 302 of the integration server 30 according to an instruction of the master model learning management program 33.

In step S31, the processor 302 receives the learning result and the metadata accompanying the learning result from each client 20.

In step S32, the processor 302 associates and stores the learning result transmitted from each client 20 with the metadata.

In step S33, the processor 302 creates the classification of similar imaging conditions based on the stored learning result and metadata. In step S34, the processor 302 creates the client cluster for each of the classified imaging condition categories.

In step S35, the processor 302 integrates the learning results for each client cluster to create the master model candidate MMC from each client cluster. In a case where the plurality of master model candidates MMC are created in step S35, the processor 302 stores the information indicating the correspondence relationship as to from which client cluster each master model candidate MMC is created in the data storage unit such as the database 326. The relationship between the client cluster and the master model candidate MMC is maintained until the subsequent training of the master model candidate MMC is ended.

In step S36, the processor 302 evaluates the inference accuracy for each of the created master model candidates MMC. That is, the processor 302 causes the master model candidate MMC to perform the inference by using, as an input, the verification data TD for each imaging condition prepared in advance to calculate the inference accuracy, and compares the inference accuracy with the accuracy target value. Further, the processor 302 stores, in the database 326, the calculated inference accuracy and the comparison result between the inference accuracy and the accuracy target value in association (correlation) with the master model candidate MMC.

For the inference accuracy of the master model candidate that is to be compared with the accuracy target value when performing processing of step S36, an instantaneous value or a statistical value such as an average value or a median value is used as an appropriate value. An example of processing contents in the inference accuracy evaluation applied to step S36 will be described later with reference to FIG. 9.

In step S37, the processor 302 determines whether or not a master model candidate MMC having an inference accuracy higher than the accuracy target value is obtained. In a case where a determination result in step S37 is Yes, that is, in a case where the inference accuracy of the master model candidate MMC exceeds the accuracy target value, the processor 302 ends the training of the master model candidate MMC (step S38) and sends notification of the end of the learning thereof (step S39).

For example, in step S38, the processor 302 sets a master model candidate MMC having the inference accuracy higher than the accuracy target value, as the latest model having improved performance after learning, stores the model in the data storage unit such as the database 326 in an appropriate format such as a file, and sends notification that learning is ended. Here, as a notification method, a message queue, a general inter-process communication, or the like may be used. The notification that the learning is ended may be displayed on the display device 316 or may be transmitted to the client 20.

On the other hand, in a case where the determination result in step S37 is No, that is, in a case where the master model candidate MMC having an inference accuracy higher than the accuracy target value is not obtained, the processor 302 proceeds to step S40.

In step S40, the processor 302 synchronizes, using the correspondence information stored in step S35, the local model LM of the client cluster used to create the master model candidate MMC that has not reached the target accuracy with the master model candidate MMC, causes the corresponding client 20 to repeat the local learning (refer to FIG. 7), and repeats steps S31 to S40.

In step S40, the processor 302 may set the master model candidate MMC having the highest inference accuracy that is found in the repetition of step S31 to step S40 as a provisional master model and synchronize the model with the local model LM of the client.

<<Example of Inference Accuracy Evaluation Processing>>

FIG. 9 is a flowchart illustrating an example of processing of evaluating an inference accuracy of the master model candidate MMC in the integration server 30. The flowchart illustrated in FIG. 9 is applied to step S36 of FIG. 8. Here, the inference accuracy evaluation processing is described for one master model candidate MMC. However, the same processing is performed for each master model candidate MMC created from each of the plurality of client clusters in which the combination of the clients 20 is different for each imaging condition category.

In step S341 of FIG. 9, the processor 302 causes the master model candidate MMC to execute the inference with the verification data TD for each imaging condition as an input.

In step S342, the processor 302 calculates an inference accuracy of the master model candidate MMC based on the inference result and the correct answer data.

In step S343, the processor 302 compares the inference accuracy of the master model candidate MMC with an accuracy target value. Here, the accuracy target value may be compared with an instantaneous value of the inference accuracy of the master model candidate MMC. However, in the comparison, while maintaining the configuration of the client cluster used for the creation of the master model candidate MMC, the procedures of steps S31 to S343 may be performed for several iterations, the inference accuracy at that time may be recorded each time, and a statistical value such as an average value or a median value of the inference accuracy may be compared with the accuracy target value.

In step S344, the processor 302 stores the inference accuracy of the master model candidate MMC and the comparison result between the inference accuracy and the accuracy target value in the database 326.

After step S344, the processor 302 ends the flowchart of FIG. 9 and returns to the flowchart of FIG. 8.

<<Specific Example of Processing by Cooperation of Integration Server 30 and Plurality of Clients 20>>

Here, a specific example of processing performed by the integration server 30 and the plurality of clients 20 will be described. In the example, it is assumed that the plurality of clients 20 are a plurality of CAD servers 60 illustrated in FIG. 4. The integration server 30 and the plurality of CAD servers 60 execute processing of [Procedure 301] to [Procedure 307] to be described below.

[Procedure 301] The distribution learning client program is executed on the CAD server 60 in the medical institution network 50 of each of the plurality of medical institutions.

[Procedure 302] The integration server 30 stores the imaging apparatus information of the learning client group. The integration server 30 extracts the required number of a part of the client group (client cluster) used for the learning for each similar imaging apparatus from the client group including the innumerable clients 20, which is the client population, to create a plurality of client groups for each similar imaging apparatus. Here, the term "for each similar imaging apparatus" may be, for example, an imaging apparatus group having the same model number series of the apparatus. The classification "for each similar imaging apparatus" is a form of the classification "for each similar imaging condition". Here, an example of classifying according to the type (model) of the apparatus which is the "imaging apparatus" is described. Similar imaging conditions may be defined according to conditions of a combination of the model and the imaging condition to classify the imaging condition categories.

[Procedure 303] The client 20 for the distribution learning in each client cluster performs iterations for learning a set number of times using data (for example, a medical image) in the medical institution network to which the client 20 belongs and information accompanying the data.

[Procedure 304] Each client 20 transmits the weight parameter of the trained learning model to the integration server 30 via the wide area communication line 70.

An attached document of a medical apparatus as the client 20 that uses the function according to the present embodiment describes that learning is performed as background processing within a range in which the learning does not interfere with medical work. In addition, the attached document describes that learning data to be used is data in the medical institution, that data to be transmitted to the outside is only a weight parameter after learning, and that data by which an individual is identified is not transmitted.

[Procedure 305] The integration server 30 collects the weight parameters of the learning results transmitted from the client 20 for each client cluster, and creates a master model candidate MMC for each client cluster.

[Procedure 306] The integration server 30 performs the accuracy verification of each master model candidate MMC created for each client cluster. The accuracy verification may be paraphrased as "accuracy evaluation". The integration server 30 causes the master model candidate MMC to perform an inference using the verification data TD and compares an inference result with the correct answer data. The verification data TD is prepared for each similar imaging apparatus. The accuracy verification is performed by using an image captured by an imaging apparatus that is the same as or similar to the imaging apparatus that captures the image of the learning data used to create the master model candidate MMC.

[Procedure 307] The integration server 30 confirms the inference accuracy of the model having the highest inference accuracy among the master model candidates MMC created for each client cluster. In a case where the highest inference accuracy is higher than the target accuracy (accuracy target value), the master model candidate MMC having the highest accuracy (maximum inference accuracy) is adopted as a product model.

On the other hand, in a case where the inference accuracy of the master model candidate MMC with the highest accuracy is lower than the accuracy target value, the integration server 30 performs the learning iteration from procedure 303 to procedure 307 again using the client cluster with higher accuracy.

The integration server 30 performs the learning iteration from procedure 303 to procedure 307 until the master model candidate MMC having the inference accuracy higher than the accuracy target value is obtained. Alternatively, in a case where the master model candidate MMC having an inference accuracy higher than the accuracy target value is not obtained even though iterations are performed by the designated upper limit number of iterations, the integration server 30 may adopt the master model candidate MMC from which the maximum inference accuracy is obtained in the search process so far, as the product model.

In this way, in the new master model created by performing the machine learning method using the machine learning system 10 according to the present embodiment, the inference accuracy is improved as compared with the master model before the learning.

According to the present embodiment, it is possible to update an inference performance of the master model MM. In a case where the new master model created by performing the machine learning method according to the present embodiment is provided by sales or the like, preferably, the number of the clients used for the learning, the number of pieces of verification data used for verification of the accuracy, and the like are described in an attached document provided in sales. For the number of the clients used for the learning, for example, the classification of the clients is preferably displayed such as "hospital_how many cases", "clinic with bed_how many cases", and "clinic without bed_how many cases" as a client profile.

As a preliminary procedure in a case where a version of the master model as a current product is upgraded, information indicating the inference accuracy in the previous version and the inference accuracy in the new version and information indicating the number of the clients used for additional learning and the classification of the clients are presented to a medical institution, and an approval is received from the medical institution before the version is upgraded. After the approval is obtained, the version is upgraded.

<<Example of Hardware Configuration of Computer>>

FIG. 10 is a block diagram illustrating an example of a hardware configuration of a computer. A computer 800 may be a personal computer, a workstation, or a server computer. The computer 800 may be used as a part or all of the client 20, the integration server 30, the PACS server 58, the CAD server 60, and the terminal 62 described above, or may be used as an apparatus having a plurality of functions thereof.

The computer 800 comprises a central processing unit (CPU) 802, a random access memory (RAM) 804, a read only memory (ROM) 806, a graphics processing unit (GPU) 808, a storage 810, a communication unit 812, an input device 814, a display device 816, and a bus 818. The GPU 808 may be provided as necessary.

The CPU 802 reads out various programs stored in the ROM 806, the storage 810, or the like, and executes various processing. The RAM 804 is used as a work area of the CPU 802. Further, the RAM 804 is used as a storage unit for temporarily storing the read program and various data.

The storage 810 includes, for example, a hard disk apparatus, an optical disk, a magneto-optical disk, a semiconductor memory, or a storage device configured by using an appropriate combination thereof. The storage 810 stores various programs, data, and the like required for inference processing and/or learning processing. The program stored in the storage 810 is loaded into the RAM 804, and the CPU 802 executes the program. Thus, the computer 800 functions as means for performing various processing defined by the program.

The communication unit 812 is an interface that performs communication processing with an external apparatus in a wired manner or a wireless manner and exchanges information with the external apparatus. The communication unit 812 may play a role of an information acquisition unit that receives an input such as an image.

The input device 814 is an input interface that receives various operation inputs to the computer 800. The input device 814 is configured with, for example, a keyboard, a mouse, a touch panel, another pointing device, a voice input device, or an appropriate combination thereof.

The display device 816 is an output interface for displaying various information. The display device 816 is configured with, for example, a liquid crystal display, an organic electro-luminescence (OEL) display, a projector, or an appropriate combination thereof.

<<Program for Operating Computer>>

A program causing a computer to realize a part or all of at least one processing function among various processing functions, such as the learning data classification function and the local learning function in each client 20 and the master model learning management function including the client cluster creation function, the master model candidate creation function, and the inference accuracy evaluation function in the integration server 30, described in the embodiment may be recorded on a computer-readable medium as a non-transitory tangible information storage medium, such as an optical disk, a magnetic disk, or a semiconductor memory, and the program may be provided with the information storage medium.

Further, instead of the form in which the program is provided by being stored in a non-transitory tangible computer-readable medium, a program signal may be provided as a download service using a telecommunication line such as the Internet.

A service may be possible in which a part or all of at least one processing function among the various processing functions, such as the learning data classification function and the local learning function and the master model learning management function including the client cluster creation function, the master model candidate creation function, and the inference accuracy evaluation function, described in the embodiment is provided as an application server and the processing function is provided via a telecommunication line.

<<Hardware Configuration of Each Processing Unit>>

As a hardware structure of the processing units that execute various pieces of processing, such as the imaging condition classification unit 332 and the master model candidate creation unit 334 illustrated in FIG. 3, the master model storage unit 320, the verification data storage unit 322, the imaging apparatus information storage unit 324, the master model learning management unit 330, the client cluster creation unit 333, the inference accuracy evaluation unit 340, the inference unit 342, the inference accuracy calculation unit 344, the accuracy target value comparison unit 346, and the display control unit 350 illustrated in FIG. 5, and the synchronization processing unit 631, the learning data classification processing unit 632, the learning data acquisition unit 633, the local model LM, the error calculation unit 634, the optimizer 635, the learning result storage unit 636, the transmission processing unit 637, the AI-CAD unit 642, and the display control unit 650 illustrated in FIG. 6, for example, the following various processors may be used.

The various processors include a CPU which is a general-purpose processor that functions as various processing units by executing a program, a GPU which is a processor specialized for image processing, a programmable logic device (PLD) such as a field programmable gate array (FPGA) which is a processor capable of changing a circuit configuration after manufacture, a dedicated electric circuit such as an application specific integrated circuit (ASIC) which is a processor having a circuit configuration specifically designed to execute specific processing, and the like.

One processing unit may be configured by one of these various processors or may be configured by two or more processors having the same type or different types. For example, one processing unit may be configured by a plurality of FPGAs, a combination of a CPU and an FPGA, or a combination of a CPU and a GPU. Further, the plurality of processing units may be configured by one processor. As an example in which the plurality of processing units are configured by one processor, firstly, as represented by a computer such as a client and a server, a form in which one processor is configured by a combination of one or more CPUs and software and the processor functions as the plurality of processing units may be adopted. Secondly, as represented by a system on chip (SoC) or the like, a form in which a processor that realizes the function of the entire system including the plurality of processing units by one integrated circuit (IC) chip is used may be adopted. As described above, the various processing units are configured by using one or more various processors as a hardware structure.

Further, as the hardware structure of the various processors, more specifically, an electric circuit (circuitry) in which circuit elements such as semiconductor elements are combined may be used.

Advantages According to Present Embodiment

According to the machine learning system 10 according to the embodiment of the present invention, the following advantages are obtained.

[1] Learning can be performed without extracting personal information such as a diagnosis image that requires consideration for privacy from a medical institution.

[2] A data group used for learning is classified into a data group with substantially uniform conditions (imaging condition category grouped as similar imaging conditions) from the viewpoint of imaging conditions, and the learning is performed using homogenized learning data. Therefore, effective learning is possible.

[3] In federated learning, there is provided a mechanism for optimizing the combination of the clients 20 used for creation of a new model by integrating the learning results. Accordingly, as compared with a method of collecting and integrating the learning results of all the clients 20 into one or a method of randomly extracting a combination from the client population, it is possible to select a client group that is effective in improving the accuracy and to realize the high inference accuracy at an early stage.

[4] It is possible to create an AI model having a high inference accuracy.

Modification Example 1

In the embodiment, the AI model for medical image diagnosis has been described as an example. However, the scope of application of the technique of the present disclosure is not limited to this example. For example, the present disclosure may be applied even in a case where learning is performed on an AI model using time-series data as input data or an AI model using document data as input data. The time-series data may be, for example, electrocardiogram waveform data. The document data may be, for example, a diagnosis report, and the present disclosure may be applied to training of an AI model for supporting creation of a report. The electrocardiogram waveform data is an example of "inspection data" in the present disclosure.

The data used for the learning may be a combination of different types of data acquired by different modalities. The condition category set as "the same or a similar condition" in the case may be set depending on the combination of data acquisition conditions in the different modalities.

The data used for the learning may be a combination of a plurality of types of different data, such as a combination of images and time-series data or a combination of images and document data. In a case where data other than the image, such as electrocardiogram waveform data, is used for the learning, the terms "similar imaging condition", "imaging condition category", and "imaging apparatus" described in the embodiment can be extended to terms such as "similar inspection condition", "inspection condition category", and "inspection apparatus", and the extended terms can be applied to the configuration of the embodiment.

Modification Example 2

In the embodiment, an example in which an accuracy target value by learning is set and the inference accuracy of the master model candidate is compared with the accuracy target value has been described. However, the accuracy target value may be updated as necessary. Instead of or in combination with the comparison with the accuracy target value, the learning may proceed under a condition that the inference accuracy of the model is maximized within the time limit or the designated number of iterations.

<<Other>>

The matters described in the configuration and the modification example described in the embodiment may be used in combination as appropriate, and some matters may be replaced. The present invention is not limited to the embodiment described above, and various modifications may be made without departing from the scope of the present invention.

EXPLANATION OF REFERENCES

10: machine learning system
20: client
21: local learning management program
30: integration server
33: master model learning management program
50: medical institution network
52: CT apparatus
54: MRI apparatus
56: CR apparatus
58: PACS server
60: CAD server
62: terminal
64: internal communication line
70: wide area communication line
80: learning data storage unit
302: processor
304: computer-readable medium
306: communication interface
308: input/output interface
310: bus
314: input device
316: display device
320: master model storage unit
322: verification data storage unit
324: imaging apparatus information storage unit
326: database
328: synchronization program
330: master model learning management unit
332: imaging condition classification unit
333: client cluster creation unit
334: master model candidate creation unit
340: inference accuracy evaluation unit
342: inference unit
344: inference accuracy calculation unit
346: accuracy target value comparison unit
350: display control unit
602: processor
604: computer-readable medium
606: communication interface
608: input/output interface
610: bus
614: input device 616: display device
630: local learning management program
631: synchronization processing unit
632: learning data classification processing unit
633: learning data acquisition unit
634: error calculation unit
635: optimizer
636: learning result storage unit
637: transmission processing unit
640: diagnosis support program
642: AI-CAD unit
650: display control unit
800: computer
802: CPU
804: RAM
806: ROM
808: GPU
810: storage
812: communication unit
814: input device
816: display device
818: bus
CL1 to CL4, CLN, CLN+1: client
LD, LD1, LD11, LD12: local data
LD2, LD21, LD23, LD24: local data
LD3, LD32, LD33: local data
LM, LM11, LM12: local model
LM21, LM23, LM24, LM32, LM33: local model
MM: master model
MMC: master model candidate
TD: verification data
S21 to S25: steps of local learning management processing
S31 to S40: steps of master model learning management processing
S341 to S344: steps of inference accuracy evaluation processing

What is claimed is:

1. A machine learning system comprising:
a plurality of client terminals; and
an integration server,
wherein each of the plurality of client terminals includes
a terminal-side processor configured to:
classify data stored in a data storage apparatus of a medical institution based on an acquisition condition of the data to classify learning data into each data group acquired under the same or a similar acquisition condition, the acquisition condition including condition concerning apparatus used to generate the data;
execute machine learning of a learning model for each learning data group classified into each condition category of the same or a similar acquisition condition; and
transmit learning results of the learning model executed for each learning data group and condition information regarding the acquisition condition of the learning data group used for the learning, to the integration server, and
the integration server includes
a trained master model, and
a server-side processor configured to:
synchronize the learning model of each client terminal side with the master model before each of the plurality of client terminals trains the learning model;
receive the learning results of the learning model and the condition information from each of the plurality of client terminals;
classify the learning results into each condition category;
integrate the learning results for each condition category to create a plurality of master model candidates; and
evaluate an inference accuracy of each of the plurality of master model candidates,
wherein the data includes inspection data acquired by using an inspection apparatus, and the acquisition condition includes an inspection condition under which the inspection data is acquired,
wherein the inspection condition includes condition concerning the inspection apparatus used for inspection.

2. The machine learning system according to claim 1, wherein
the data includes an image captured by using an imaging apparatus, and
the acquisition condition includes an imaging condition for the image.

3. The machine learning system according to claim 2, wherein the imaging condition includes a condition regarding a model of the imaging apparatus used for imaging.

4. The machine learning system according to claim 2, wherein the imaging condition includes a condition of an imaging parameter settable at a time of imaging.

5. The machine learning system according to claim 1, wherein
the inspection condition includes condition concerning inspection parameter settable at a time of inspection.

6. The machine learning system according to claim 1, wherein
the acquisition condition includes a condition regarding a value of a parameter settable in an apparatus used to obtain the data, and
the terminal-side processor classifies acquisition conditions in which a specific value of the parameter, which is a specific acquisition condition, is within a designated value range into the condition category in which the acquisition conditions are handled as the acquisition condition that is the same as or similar to the specific acquisition condition.

7. The machine learning system according to claim 1, wherein
a combination of conditions in which a plurality of acquisition conditions are handled as a similar condition is designated, and
the terminal-side processor performs the classification into the condition category according to a setting of the designated similar condition.

8. The machine learning system according to claim 1, wherein each of the plurality of client terminals is a terminal provided in a medical institution network of a different medical institution.

9. The machine learning system according to claim 1, wherein
the integration server is provided in a medical institution network or outside the medical institution network.

10. The machine learning system according to claim 1, wherein the learning results transmitted from the client terminal to the integration server include a weight parameter of the learning model after the learning.

11. The machine learning system according to claim 1, wherein the data used as the learning data includes at least one type of data among a two-dimensional image, a three-dimensional image, a moving image, time-series data, or document data.

12. The machine learning system according to claim 1, wherein each model of the learning model, the master model, and the master model candidate is configured by using a neural network.

13. The machine learning system according to claim 1, wherein
the data used as the learning data includes a two-dimensional image, a three-dimensional image, or a moving image, and
each model of the learning model, the master model, and the master model candidate is configured by using a convolutional neural network.

14. The machine learning system according to claim 1, wherein
the data used as the learning data includes time-series data or document data, and
each model of the learning model, the master model, and the master model candidate is configured by using a recurrent neural network.

15. The machine learning system according to claim 1, wherein the integration server includes an information storage that stores information indicating a correspondence relationship as to which client cluster among a plurality of client clusters each of the plurality of master model candidates created is based on.

16. The machine learning system according to claim 1, wherein the integration server includes a display on which information indicating a progress status of learning of each of the master model candidates is displayed.

17. The machine learning system according to claim 1, further comprising:
a verification data storage that stores verification data classified based on a data acquisition condition,
wherein the server-side processor evaluates the inference accuracy of the master model candidate using the verification data.

18. The machine learning system according to claim 1, wherein
the server-side processor is further configured to
compare an inference result output from the master model candidate by inputting verification data to the master model candidate with correct answer data of the verification data and calculate the inference accuracy of the master model candidate, and
compare the inference accuracy of the master model candidate with an accuracy target value.

19. A machine learning method using a plurality of client terminals and an integration server, the method comprising:
classifying, via each of the plurality of client terminals, data stored in a data storage apparatus of each of different medical institutions based on an acquisition condition of the data to classify learning data into each data group acquired under the same or a similar acquisition condition, the acquisition condition including condition concerning apparatus used to generate the data;
synchronizing a learning model of each client terminal side with a trained master model stored in the integration server before each of the plurality of client terminals trains the learning model;
executing, via each of the plurality of client terminals, machine learning of the learning model for each learning data group classified into each condition category of the same or a similar acquisition condition;
transmitting, via each of the plurality of client terminals, learning results of the learning model executed for each learning data group and condition information regarding the acquisition condition of the learning data group used for the learning, to the integration serve;
via the integration server,
receiving the learning results of the learning model and the condition information from each of the plurality of client terminals;
classifying the learning results into each condition category;
integrating the learning results for each condition category to create a plurality of master model candidates; and
evaluating an inference accuracy of each of the plurality of master model candidates,
wherein the data includes inspection data acquired by using an inspection apparatus, and the acquisition condition includes an inspection condition under which the inspection data is acquired,
wherein the inspection condition includes condition concerning the inspection apparatus used for inspection.

20. A method of creating an inference model by performing machine learning method according to claim 19, using a plurality of client terminals and an integration server, the inference model creation method comprising
creating an inference model with higher inference accuracy than the master model based on a model whose inference accuracy satisfies a target accuracy among the plurality of master model candidates.

21. An integration server connected to a plurality of client terminals via a communication line, the integration server comprising:
a first processor; and
a first computer-readable medium, which is a non-transitory tangible medium, on which a first program executed by the first processor is recorded,
wherein the first processor executes, according to an instruction of the first program, processing including
storing a trained master model on the first computer-readable medium,
synchronizing a learning model of each client terminal side with the master model before each of the plurality of client terminals trains the learning model,
receiving learning results of the learning model and condition information regarding an acquisition condition of data included in a learning data group used for the learning from each of the plurality of client terminals, the acquisition condition including condition concerning apparatus used to generate the data,
classifying the learning results into each condition category in which the acquisition condition is handled as the same or a similar condition,
integrating the learning results for each condition category to create a plurality of master model candidates, and
evaluating an inference accuracy of each of the plurality of master model candidates,
wherein the data includes inspection data acquired by using an inspection apparatus, and the acquisition condition includes an inspection condition under which the inspection data is acquired, wherein the inspection condition includes condition concerning the inspection apparatus used for inspection.

22. A non-transitory, computer-readable tangible recording medium that stores thereon a command which causes, in a case where the command is read by a computer, the computer to realize the functions of:
storing a trained master model;
synchronizing a learning model of each client terminal side with the master model before each of the plurality of client terminals trains the learning model;
receiving learning results of the learning model and condition information regarding an acquisition condition of data included in a learning data group used for the learning from each of the plurality of client terminals, the acquisition condition including condition concerning apparatus used to generate the data;
classifying the learning results into each condition category in which the acquisition condition is handled as the same or a similar condition;
integrating the learning results for each condition category to create a plurality of master model candidates; and
evaluating an inference accuracy of each of the plurality of master model candidates,
wherein the data includes inspection data acquired by using an inspection apparatus, and the acquisition condition includes an inspection condition under which the inspection data is acquired,
wherein the inspection condition includes condition concerning the inspection apparatus used for inspection.

23. An information processing apparatus used as a client terminal connected to an integration server via a communication line, the information processing apparatus comprising:
a second processor; and
a second computer-readable medium, which is a non-transitory tangible medium, on which a second program executed by the second processor is recorded,
wherein the second processor executes, according to an instruction of the second program, processing including
classifying data stored in a data storage apparatus of a medical institution based on an acquisition condition of the data to classify learning data into each data group acquired under the same or a similar acquisition condition, the acquisition condition including condition concerning apparatus used to generate the data,
executing, with a learning model synchronized with a master model stored in the integration server as the learning model in an initial state before learning starts, machine learning of the learning model for each learning data group classified into each condition category of the same or a similar acquisition condition, and
transmitting learning results of the learning model executed for each learning data group and condition information regarding the acquisition condition of the learning data group used for the learning, to the integration server,
wherein the data includes inspection data acquired by using an inspection apparatus, and the acquisition condition includes an inspection condition under which the inspection data is acquired,
wherein the inspection condition includes condition concerning the inspection apparatus used for inspection.

24. A non-transitory, computer-readable tangible recording medium that stores thereon a command which causes, in a case where the command is read by a computer, the computer to realize the functions of:
classifying data stored in a data storage apparatus of a medical institution based on an acquisition condition of the data to classify learning data into each data group acquired under the same or a similar acquisition condition, the acquisition condition including condition concerning apparatus used to generate the data;
executing, with a learning model synchronized with a master model stored in the integration server as the learning model in an initial state before learning starts, machine learning of the learning model for each learning data group classified into each condition category of the same or a similar acquisition condition; and
transmitting learning results of the learning model executed for each learning data group and condition information regarding the acquisition condition of the learning data group used for the learning, to the integration server,
wherein the data includes inspection data acquired by using an inspection apparatus, and the acquisition condition includes an inspection condition under which the inspection data is acquired,
wherein the inspection condition includes condition concerning the inspection apparatus used for inspection.

* * * * *